US012590188B2

(12) United States Patent
Ma et al.

(10) Patent No.: US 12,590,188 B2
(45) Date of Patent: Mar. 31, 2026

(54) TRI-BLOCK COPOLYMERS AND NANO-FIBROUS GELLING MICROSPHERES INCLUDING THE SAME

(71) Applicant: THE REGENTS OF THE UNIVERSITY OF MICHIGAN, Ann Arbor, MI (US)

(72) Inventors: Peter X. Ma, Ann Arbor, MI (US); Chao Zhao, Tuscaloosa, AL (US); Zhong Wang, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 999 days.

(21) Appl. No.: 17/602,678

(22) PCT Filed: Apr. 9, 2020

(86) PCT No.: PCT/US2020/027529
§ 371 (c)(1),
(2) Date: Oct. 8, 2021

(87) PCT Pub. No.: WO2020/210533
PCT Pub. Date: Oct. 15, 2020

(65) Prior Publication Data
US 2022/0162398 A1 May 26, 2022

Related U.S. Application Data

(60) Provisional application No. 62/833,002, filed on Apr. 12, 2019.

(51) Int. Cl.
*C08G 81/02* (2006.01)
*B01J 13/16* (2006.01)
*A61K 9/16* (2006.01)

(52) U.S. Cl.
CPC ............ *C08G 81/027* (2013.01); *B01J 13/16* (2013.01); *A61K 9/1647* (2013.01)

(58) Field of Classification Search
None
See application file for complete search history.

(56) References Cited

U.S. PATENT DOCUMENTS 6,201,072 B1 * 3/2001 Rathi ..................... A61K 47/34
514/12.3
7,786,220 B2 8/2010 Lee et al.
(Continued)

FOREIGN PATENT DOCUMENTS

CN 102030898 A 4/2011
CN 104072701 A 10/2014
(Continued)

OTHER PUBLICATIONS

Teodorescu, M., et al. Thermogelation properties of poly(N-isopropylacrylamide)—block—poly(ethyleneglycol)—block—poly(N-isopropylacrylamide) triblock copolymer aqueous solutions, Reactive & Punctional Polymers 70 (2010), pp. 790-797.
(Continued)

*Primary Examiner* — Anthony J Frost
(74) *Attorney, Agent, or Firm* — Dierker & Kavanaugh, P.C.

(57) ABSTRACT

A tri-block copolymer includes a first end block consisting of a hydrophobic, nano-fiber forming polymer, wherein the first end block is present in the tri-block copolymer at a weight percentage ranging from about 10% to about 89%; a middle block attached to the first end block, the middle block consisting of a hydrophilic polymer, wherein the middle block is present in the tri-block copolymer at a weight percentage ranging from about 1% to about 89%; and a second end block attached to the middle block, the second end block consisting of a temperature-responsive polymer,
(Continued)

wherein the second end block is present in the tri-block copolymer at a weight percentage ranging from about 1% to about 89%.

19 Claims, 20 Drawing Sheets

(56)                 References Cited

U.S. PATENT DOCUMENTS

| | | | |
|---|---|---|---|
| 8,591,951 | B2 | 11/2013 | Kohn et al. |
| 2003/0232088 | A1 | 12/2003 | Huang et al. |
| 2004/0213756 | A1 | 10/2004 | Michal et al. |
| 2006/0073281 | A1 | 4/2006 | Chu et al. |
| 2007/0031499 | A1 | 2/2007 | Huh et al. |
| 2008/0182959 | A1* | 7/2008 | Yang ...................... C08L 33/26 |
| | | | 527/207 |
| 2008/0293827 | A1 | 11/2008 | Lee et al. |
| 2009/0220614 | A1* | 9/2009 | Qin .................... C08F 293/005 |
| | | | 424/501 |
| 2015/0056471 | A1* | 2/2015 | Joo ................... C04B 35/63488 |
| | | | 501/153 |
| 2018/0094099 | A1 | 4/2018 | Johnson et al. |

FOREIGN PATENT DOCUMENTS

| | | |
|---|---|---|
| CN | 108530642 A | 9/2018 |
| WO | 2005035606 A1 | 4/2005 |

OTHER PUBLICATIONS

Han, H., et al. A biodegradable nanofiber by electrospinning and its cytocompatibility of Polymer-Coated Sirolimus-Eluting Stents with cardiac muscle cell, International Conference on Human Health and Biomedical Engineering, Aug. 19-22, 2011, Jilin, China, pp. 617-623.

Ueki, T., "Stimuli-responsive polymers in ionic liquids", Polymer Journal (2014) vol. 46, pp. 646-655.

Han, L., et al. "Improved Pharmacokinetics of Icariin (ICA) within Formulation of PEG-PLLA/PDLA-PNIPAM Polymeric Micelles", Pharmaceutics 2019, vol. 11, Issue 2, Article 51, 12 pages.

Wu, C., et al. "Synthesis of Stimuli Responsive Graft Triblock Polymers via Combination of Reversible Addition-Fragmentation Chain Transfer Polymerization and Ring Opening Polymerization", Asian Journal of Chemistry, vol. 25, No. 6 (2013), pp. 3344-3348.

* cited by examiner

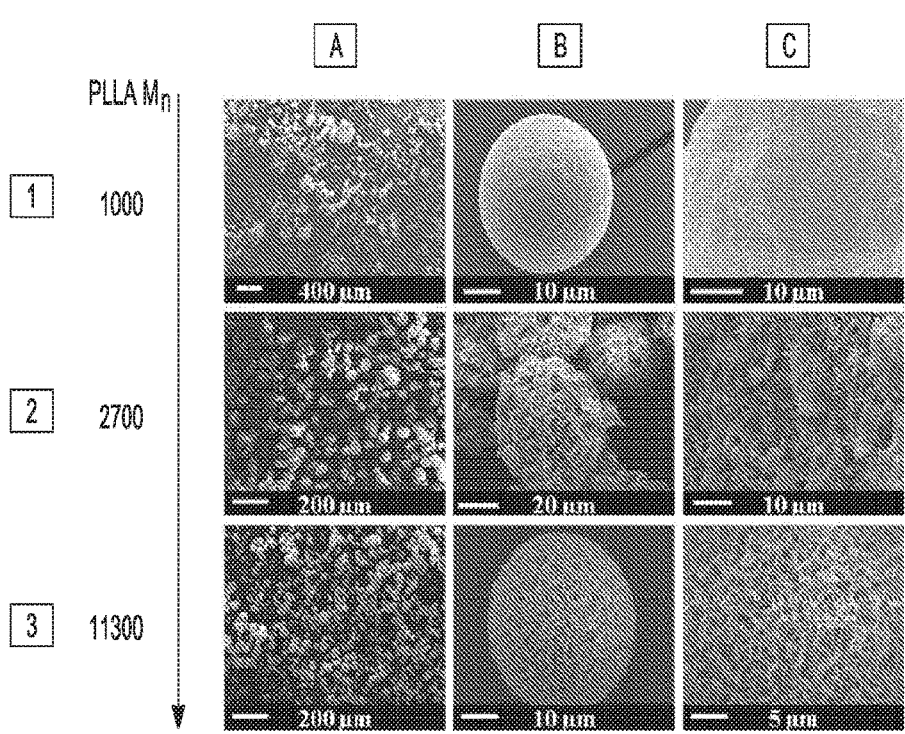
*Fig-8*
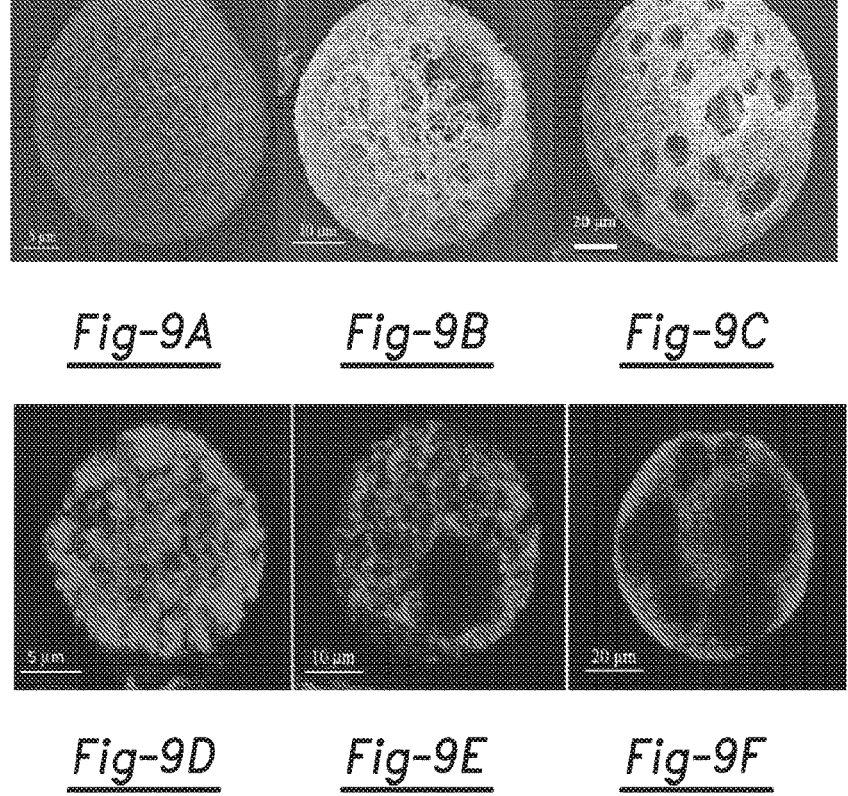
*Fig-9A*    *Fig-9B*    *Fig-9C*
*Fig-9D*    *Fig-9E*    *Fig-9F*

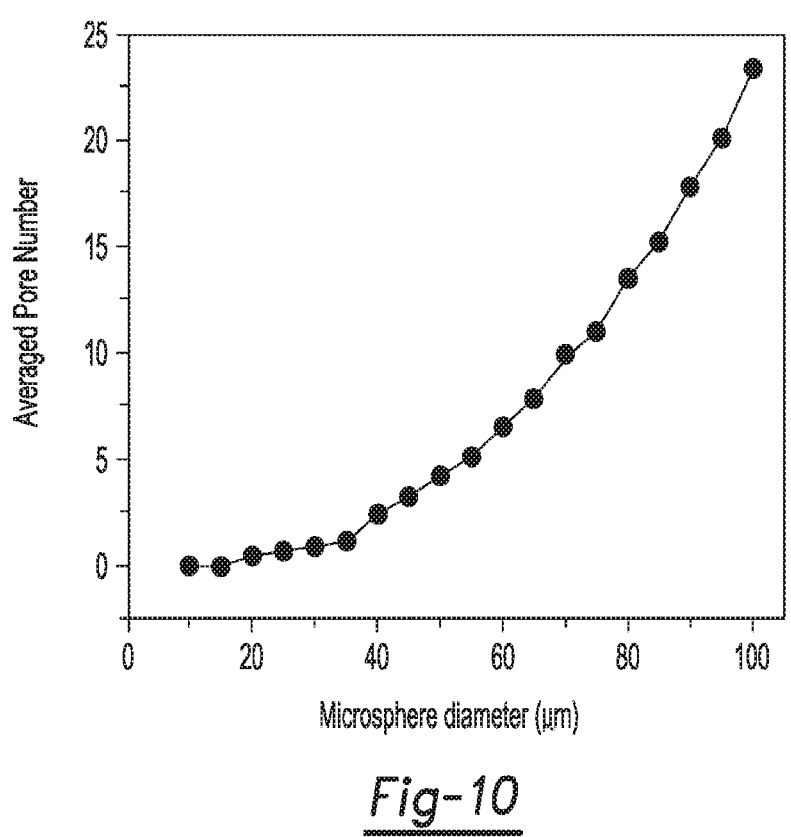
*Fig-10*
*Fig-11A*      *Fig-11B*      *Fig-11C*      *Fig-11D*
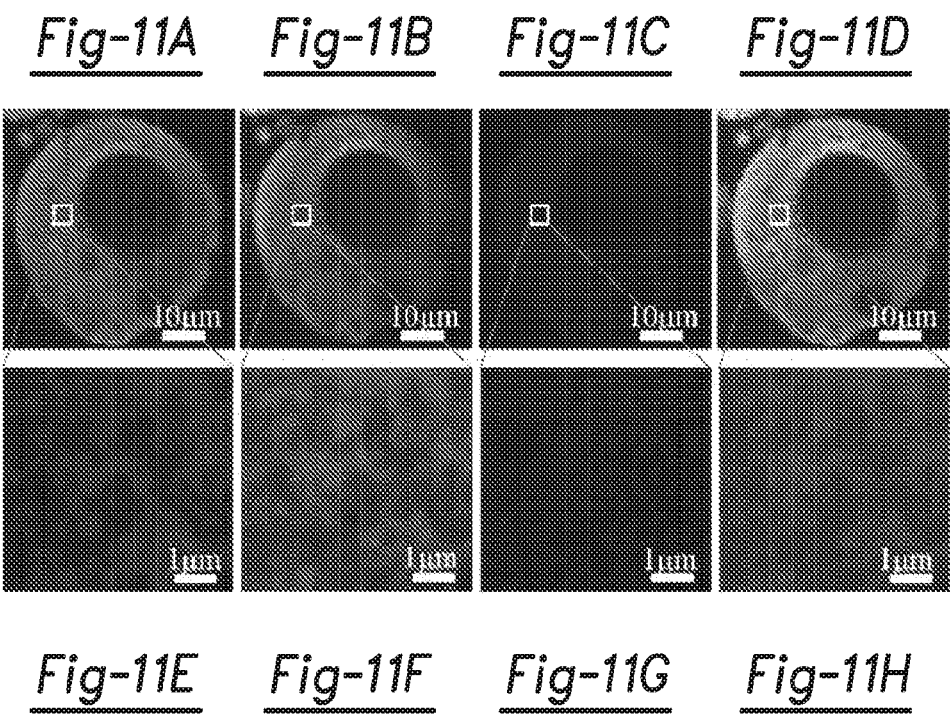
*Fig-11E*      *Fig-11F*      *Fig-11G*      *Fig-11H*

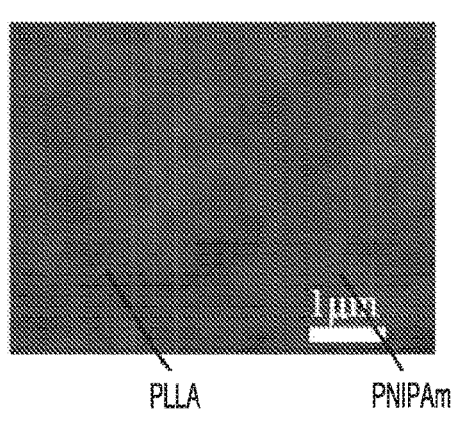
_Fig-12A_
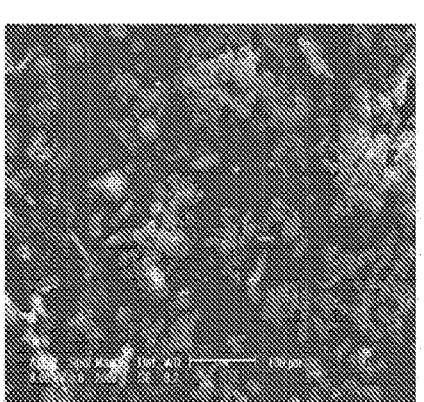
_Fig-12B_
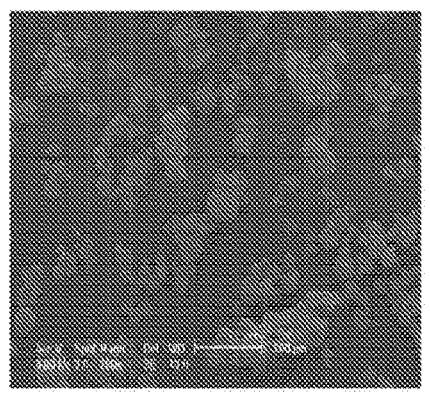
_Fig-13A_
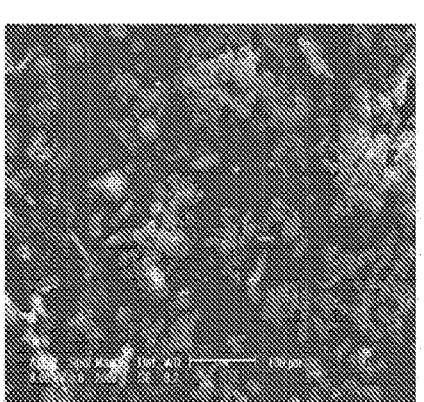
_Fig-13B_
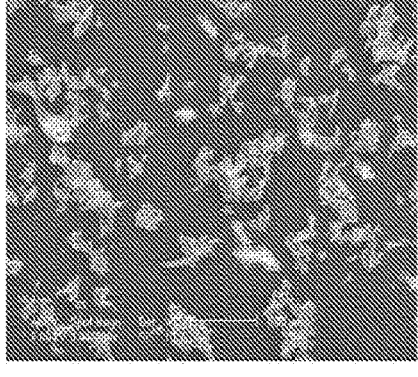
_Fig-13C_
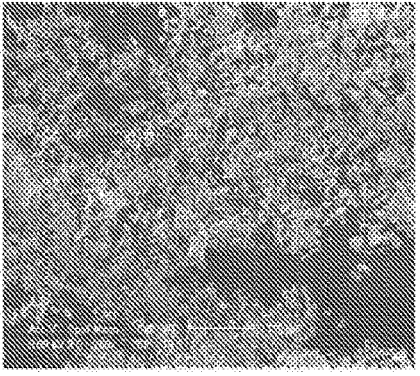
_Fig-13D_

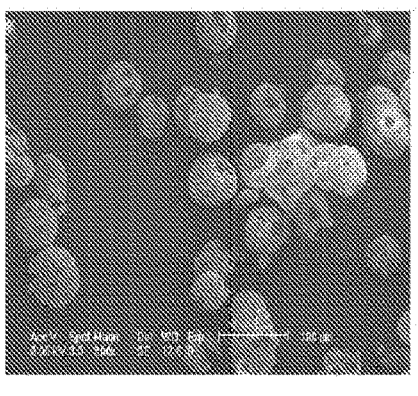
*Fig-14A*
*Fig-14B*
*Fig-14C*
*Fig-14D*
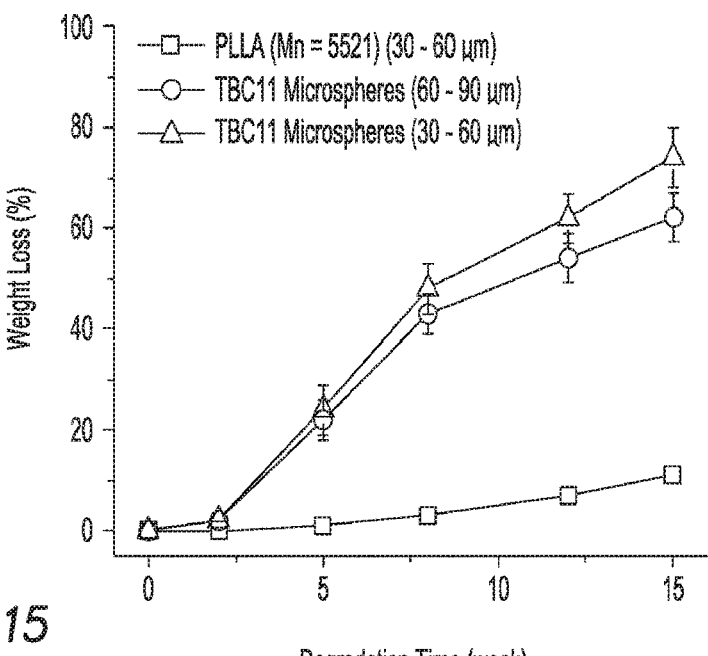
- □ — PLLA (Mn = 5521) (30 - 60 μm)
- ○ — TBC11 Microspheres (60 - 90 μm)
- △ — TBC11 Microspheres (30 - 60 μm)
Weight Loss (%)
Degradation Time (week)
*Fig-15*

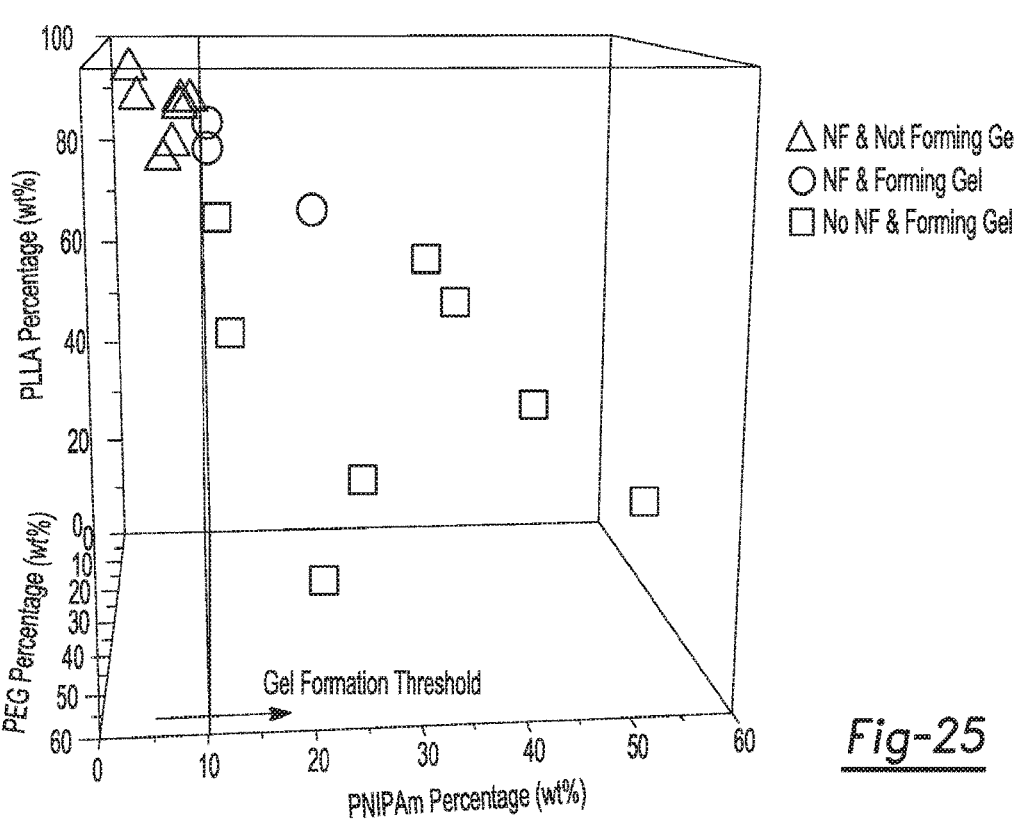
*Fig-25*
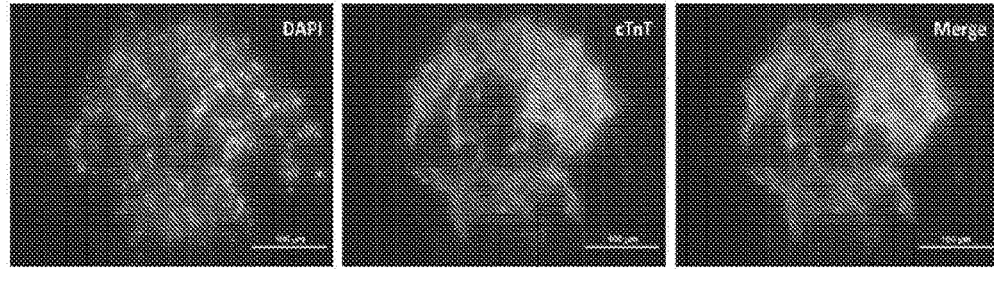
*Fig-26A*          *Fig-26B*          *Fig-26C*
CM Only          CM + NF - GMS
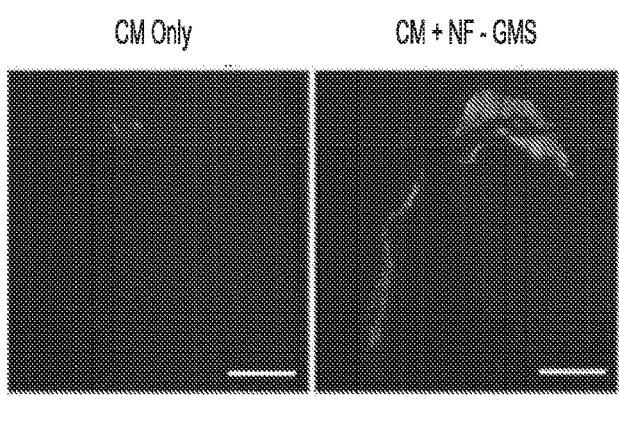
*Fig-27A*          *Fig-27B*

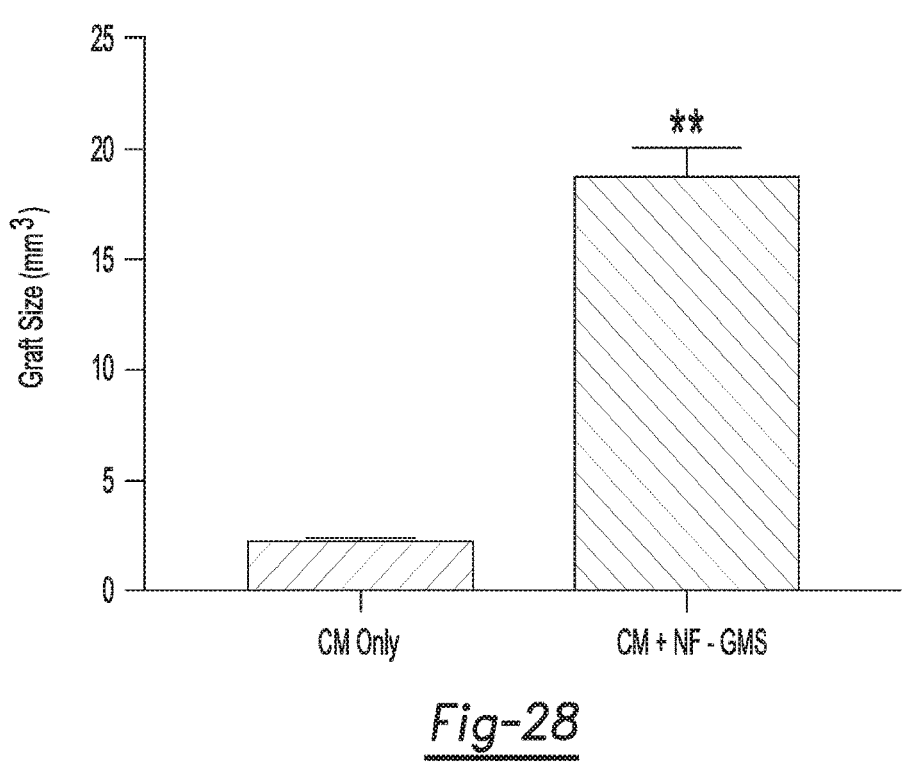
*Fig-28*
*Fig-29A*          *Fig-29B*          *Fig-29C*
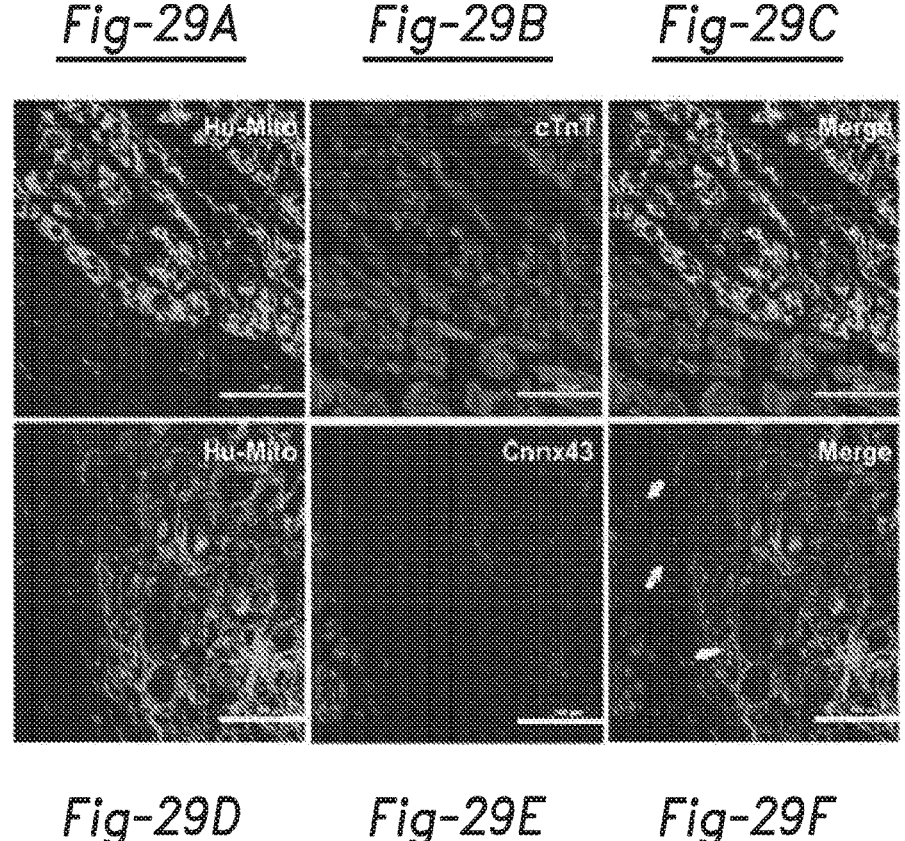
*Fig-29D*          *Fig-29E*          *Fig-29F*

*Fig-36*

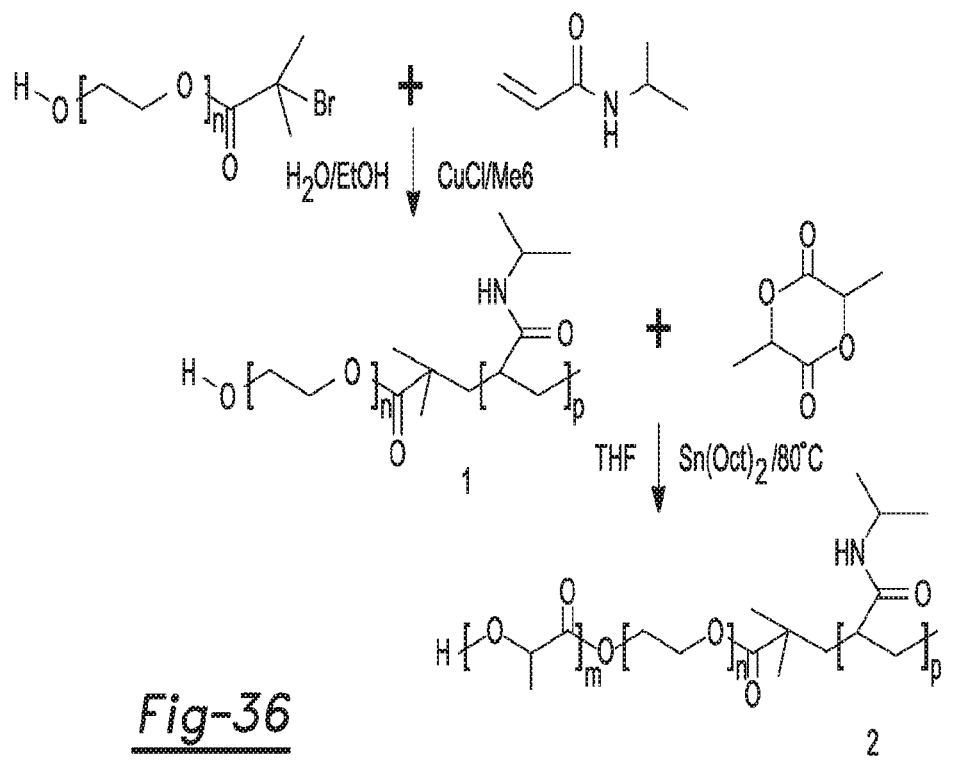

TRI-BLOCK COPOLYMERS AND NANO-FIBROUS GELLING MICROSPHERES INCLUDING THE SAME

CROSS-REFERENCE TO RELATED APPLICATIONS

This application claims the benefit of U.S. provisional application Ser. No. 62/833,002, filed Apr. 12, 2019, the contents of which is incorporated by reference herein in its entirety.

STATEMENT REGARDING FEDERALLY SPONSORED RESEARCH OR DEVELOPMENT

This invention was made with government support under HL109054, HL114038, and HL136231, awarded by the National Institutes of Health. The government has certain rights in the invention.

BACKGROUND

Regenerative medicine techniques often utilize scaffolding materials. Scaffolding materials can serve the role of three-dimensional (3D) templates. For example, scaffolds can provide appropriate pores and pore wall surfaces to foster and direct cellular attachment, migration, proliferation, differentiation, and tissue regeneration and/or organization in three dimensions. Tissue regeneration may be a potential treatment for patients with lost or diseased tissues.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIG. 8 includes black and white scanning electron microscopy (SEM) micrographs of example microspheres (30 μm to 60 μm in diameter) formed with tri-block copolymers having A1-C1) a hydrophobic block with a number average molecular weight of 1000 g/mol, A2-C2) a hydrophobic block with a number average molecular weight of 2700 g/mol, and A3-C3) a hydrophobic block with a number average molecular weight of 11300 g/mol;

FIGS. 9A through 9C are black and white SEM micrographs of microspheres formed with one example tri-block copolymer, where the different sized microspheres have A) no open hole, B) one open hole, or C) multiple open holes;

FIGS. 9D through 9F are 2D cross-sectional fluorescence micrographs (originally red in color and reproduced in black and white) of the microspheres of FIGS. 9A through 9C, respectively;

FIG. 10 is a graph of the average number of pores (Y-axis) on one side of a set of microspheres with a particular diameter (μm, X-axis), where each set included 100 microspheres for each diameter;

FIGS. 11A through 11D are black and white reproductions of 2D cross-sectional confocal fluorescence micrographs of microspheres formed with a tri-block copolymer having each of its blocks individually and chemically stained with a different fluorescent monomer, where FIG. 11A illustrates the PNIPAm block stained with Acryloxyethyl Thiocarbamoyl Rhodamine B (original image was red), FIG. 11B illustrates the PEG block stained with Fluorescein o-acrylate (original image was green), FIG. 11C illustrates the PLLA block were stained by Nile Blue Acrylamide (original image was blue), and FIG. 11D illustrates a merged fluorescence micrograph of the three blocks;

FIGS. 11E through 11H are higher magnification images of a portion of the microspheres in FIGS. 11A through 11D, respectively;

FIG. 12A is a black and white reproduction of a merged fluorescence micrograph of the PNIPAm block (FIG. 11E) and the PLLA block (FIG. 11G);

FIG. 12B is a black and white reproduction of a merged fluorescence micrograph of the PEG block (FIG. 11F) and the PLLA block (FIG. 11G);

FIGS. 13A through 13D are SEM micrographs of example microspheres (30 μm to 60 μm in diameter) formed with tri-block copolymers having PLLA:PEG:PNIPAm=68:9:23, where FIG. 13A is prior to incubation in phosphate buffered saline (PBS), FIG. 13B is 2 weeks after incubation, FIG. 13C is 5 weeks after incubation, and FIG. 13D is 8 weeks after incubation;

FIGS. 14A through 14D are SEM micrographs of example microspheres (60 μm to 90 μm in diameter) formed with tri-block copolymers having PLLA:PEG:PNIPAm=68:9:23, where FIG. 14A is prior to incubation in phosphate buffered saline (PBS), FIG. 14B is 2 weeks after incubation, FIG. 14C is 5 weeks after incubation, and FIG. 14D is 8 weeks after incubation;

FIG. 15 is a graph depicting the microsphere weight loss (%, Y-axis) versus the degradation time (in weeks) for the microspheres shown in FIGS. 13A-13D and FIGS. 14A-14D and for comparative PLLA microspheres;

Figure 18A:
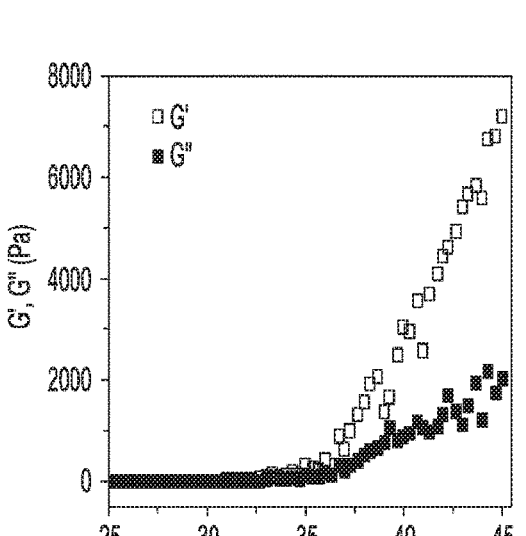
Figure 18C:
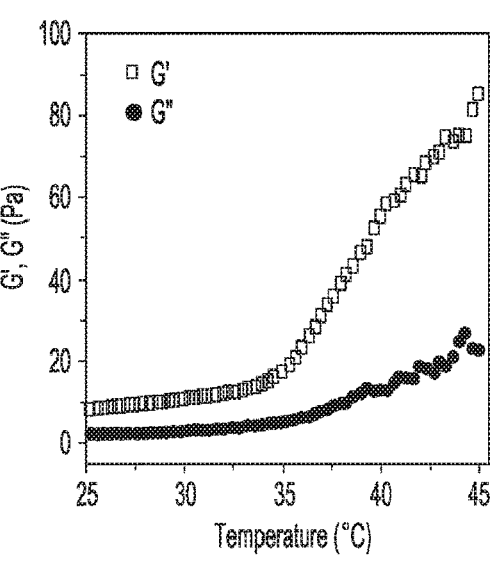
Figure 18B:
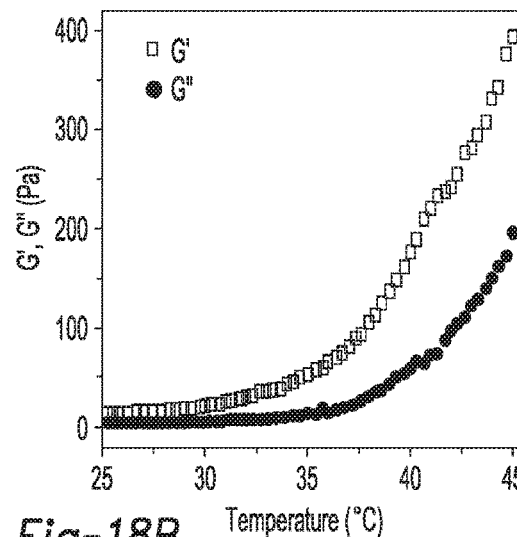
Figure 19:
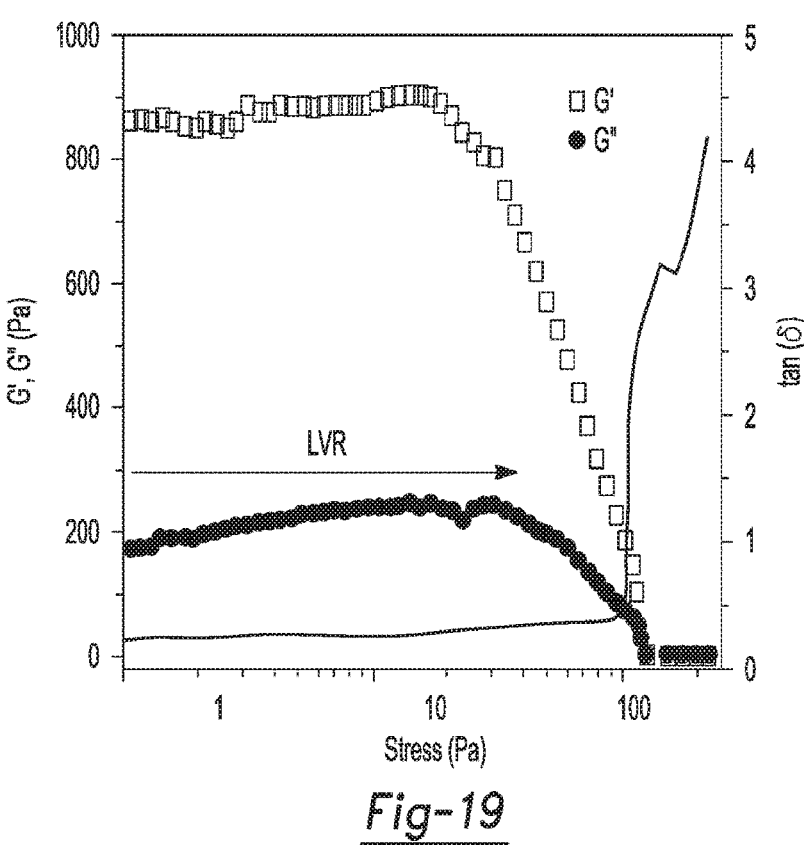
Figure 20:
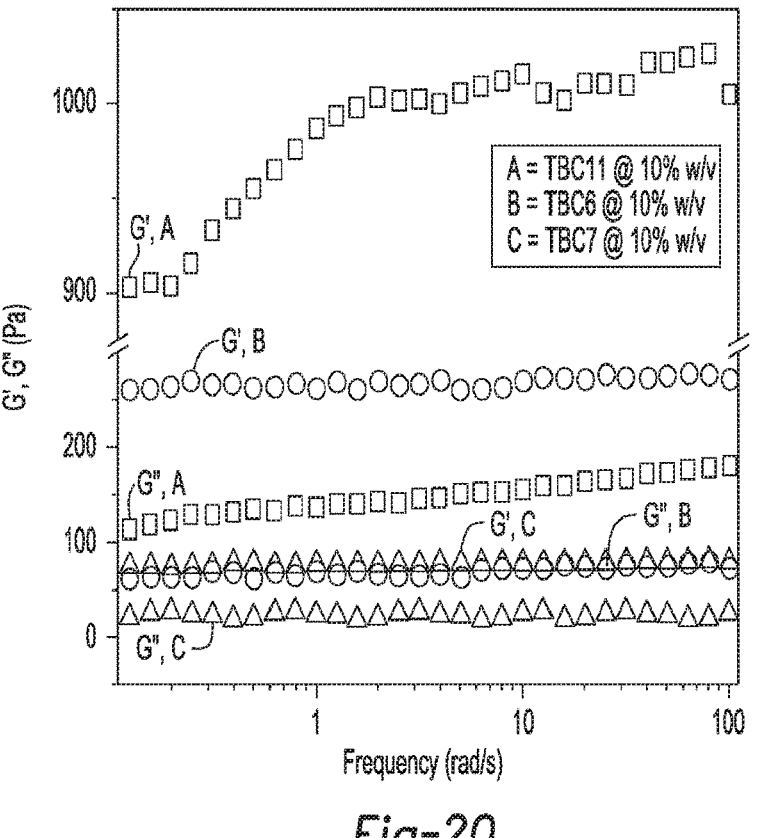
Figure 21:
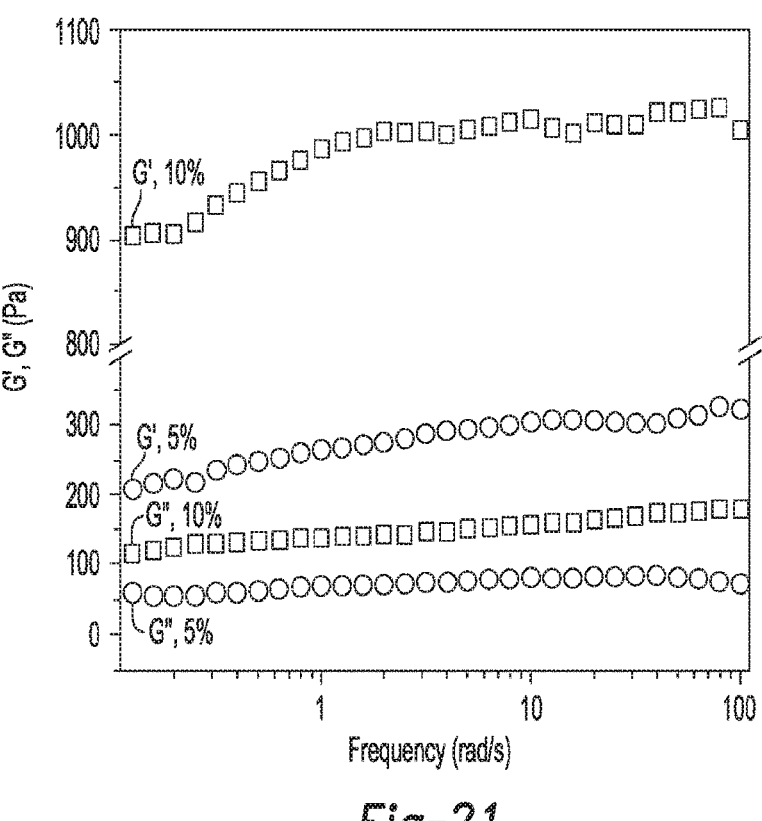
Figure 22:
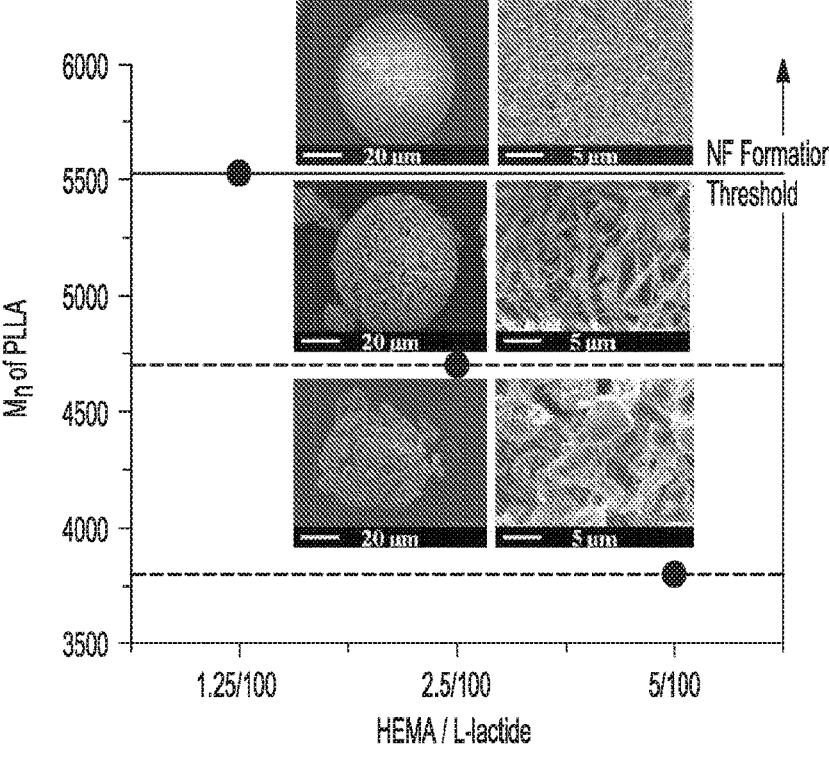
Figures 23, 24:
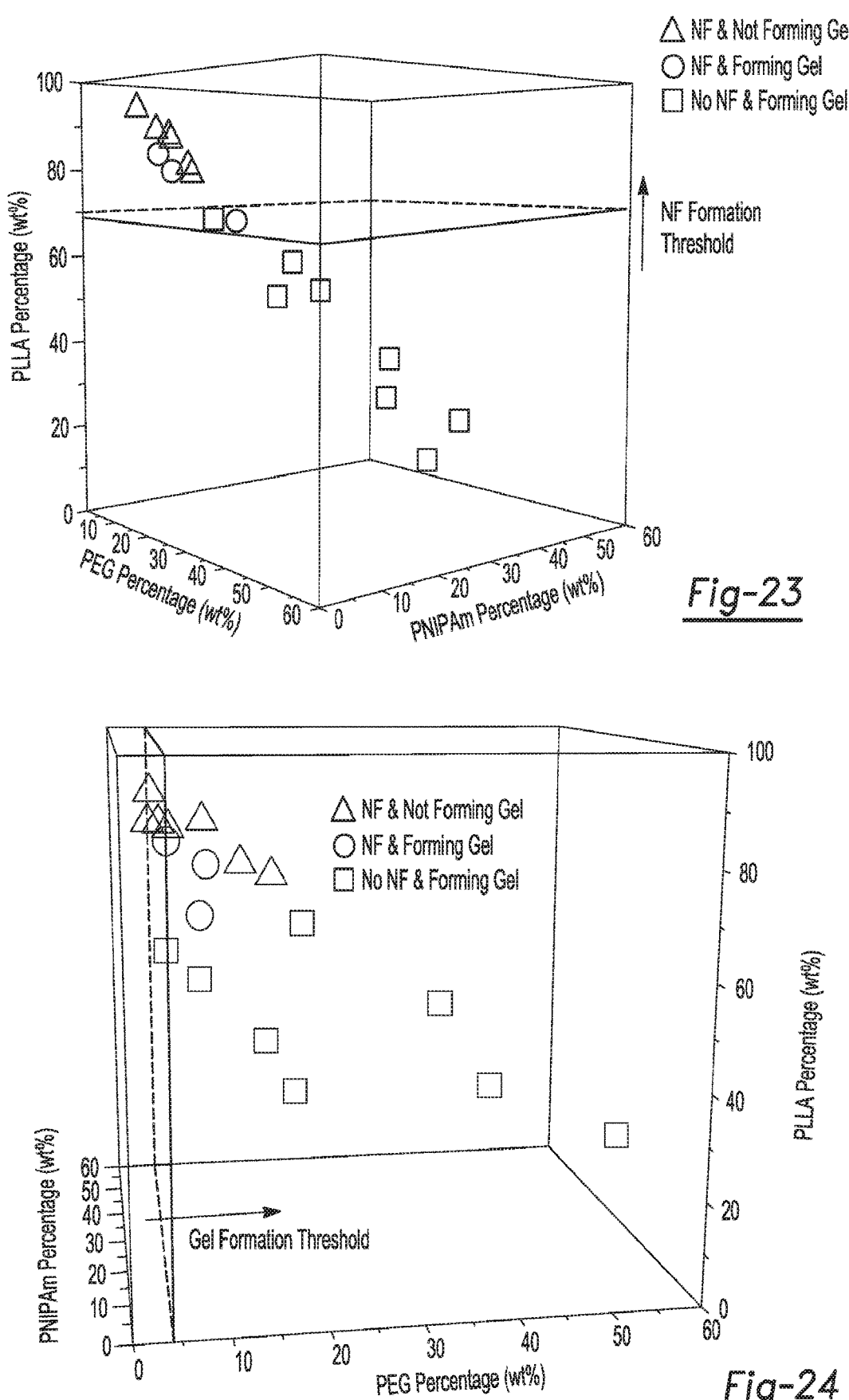

PNIPAm=68:9:23, over several different time periods, where the inset is a schematic illustration of the crosslinking of the microspheres in the hydrogel after 25 hours;

FIGS. 18A through 18C are graphs depicting the storage modulus (G') and the loss modulus (G") (both in Pa, Y-axis) versus the temperature (° C., X-axis) for: FIG. 18A—a 10% w/v aqueous suspension including PLLA:PEG:PNI-PAm=68:9:23 microspheres (TBC11, see Table 3), FIG. 18B—a 10% w/v aqueous suspension including PLLA:PEG:PNIPAm=84:5:11 microspheres (TBC6, see Table 3), and FIG. 18C—a 10% w/v aqueous suspension including PLLA:PEG:PNIPAm=88:4:8 microspheres (TBC7, see Table 3);

FIG. 19 is a graph depicting the storage modulus (G') and the loss modulus (G") (both in Pa, left Y-axis) and the ratio between the loss and storage modulus (tan(δ)=G"/G', right Y-axis) at 37° C. of the 10% w/v aqueous suspension including PLLA:PEG:PNIPAm=68:9:23 microspheres under increasing stress (in Pa, X-axis);

FIG. 20 is a graph depicting the storage modulus (G') and the loss modulus (G") (both in Pa, Y-axis) at 37° C. and under increasing frequency (rad/s, X-axis) for: A—the 10% w/v aqueous suspension including PLLA:PEG:PNI-PAm=68:9:23 microspheres (TBC11, see Table 3), B—the 10% w/v aqueous suspension including PLLA:PEG:PNI-PAm=84:5:11 microspheres (TBC6, see Table 3), and C—the 10% w/v aqueous suspension including PLLA:PEG:PNIPAm=88:4:8 microspheres (TBC7, see Table 3);

FIG. 21 is a graph depicting the storage modulus (G') and the loss modulus (G") (both in Pa, Y-axis) at a constant stress of 0.1 Pa and under increasing frequency (rad/s, X-axis) for a 5% w/v aqueous suspension including PLLA:PEG:PNI-PAm=68:9:23 microspheres (TBC11, see Table 3), and the 10% w/v aqueous suspension including PLLA:PEG:PNI-PAm=68:9:23 microspheres (TBC11, see Table 3);

FIG. 22 is a graph depicting the number average molecular weight ($M_n$) of PLLA (g/mol, Y-axis) versus the ratio of initiator (HEMA) to L-lactide, including SEM images of the microspheres formed;

FIG. 23 is a graph of the PNIPAm wt % (X-axis) versus the PEG wt % (Y-axis) versus the PLLA wt %, which illustrates the minimum PLLA wt % for nano-fiber formation;

FIG. 24 is a graph of the PEG wt % (X-axis) versus the PNIPAm wt % (Y-axis) versus the PLLA wt %, which illustrates the minimum PEG wt % for gel formation;

FIG. 25 is a graph of the PNIPAm wt % (X-axis) versus the PEG wt % (Y-axis) versus the PLLA wt %, which illustrates the minimum PNIPAm wt % for gel formation;

FIGS. 26A through 26C are black and white representations of confocal laser microscope images illustrating cardiomyocytes maintained in the hydrogel of PLLA:PEG:PNIPAm=68:9:23 (TBC11) microspheres;

FIGS. 27A and 27B are black and white representations of confocal laser microscope images illustrating cardiomyocytes (CM) engraftment, by human specific antigen (Humito) staining, in infarcted rat hearts of a group treated with CMs only (FIG. 27A) and CMs plus the TB11 microspheres (FIG. 27B);

FIG. 28 is a graph depicting the Engraft size (mm³) for a group treated with cardiomyocytes only ("CM Only") and cardiomyocytes plus the TB11 microspheres ("CM+NF-GMS") (N=9, **, P<0.01, compared with CM group);

FIGS. 29A through 29F are black and white representations of confocal laser microscope images illustrating cardiomyocytes (CM) engraftment, by immunofluorescence staining against cTnT and anti-Hu-mito staining (FIGS.

Figures 1, 2:
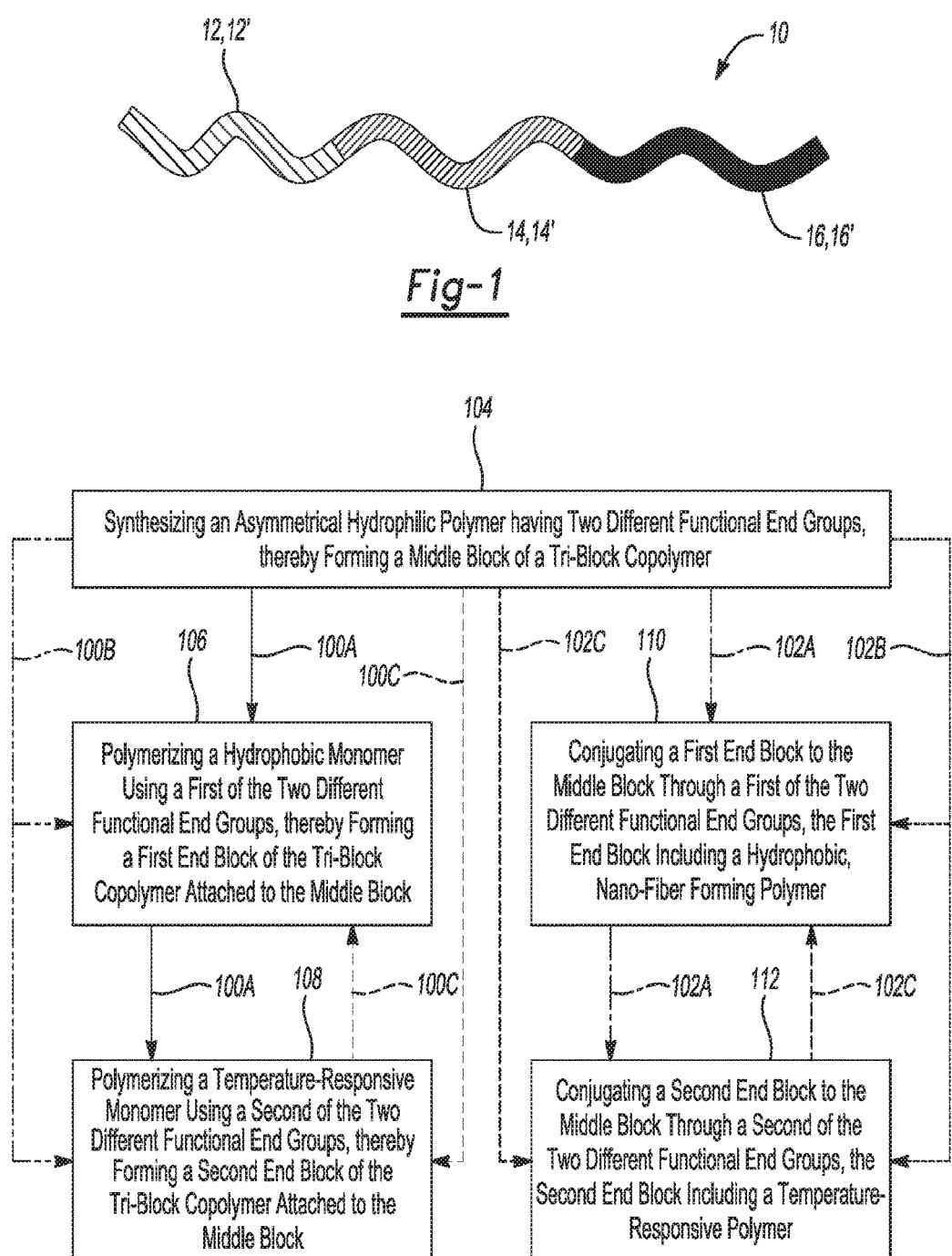
FIG. 1 is a schematic illustration of an example of the tri-block copolymer disclosed herein.
FIG. 2 is a flow diagram illustrating different examples of methods for making the tri-block copolymer.
Figure 30:
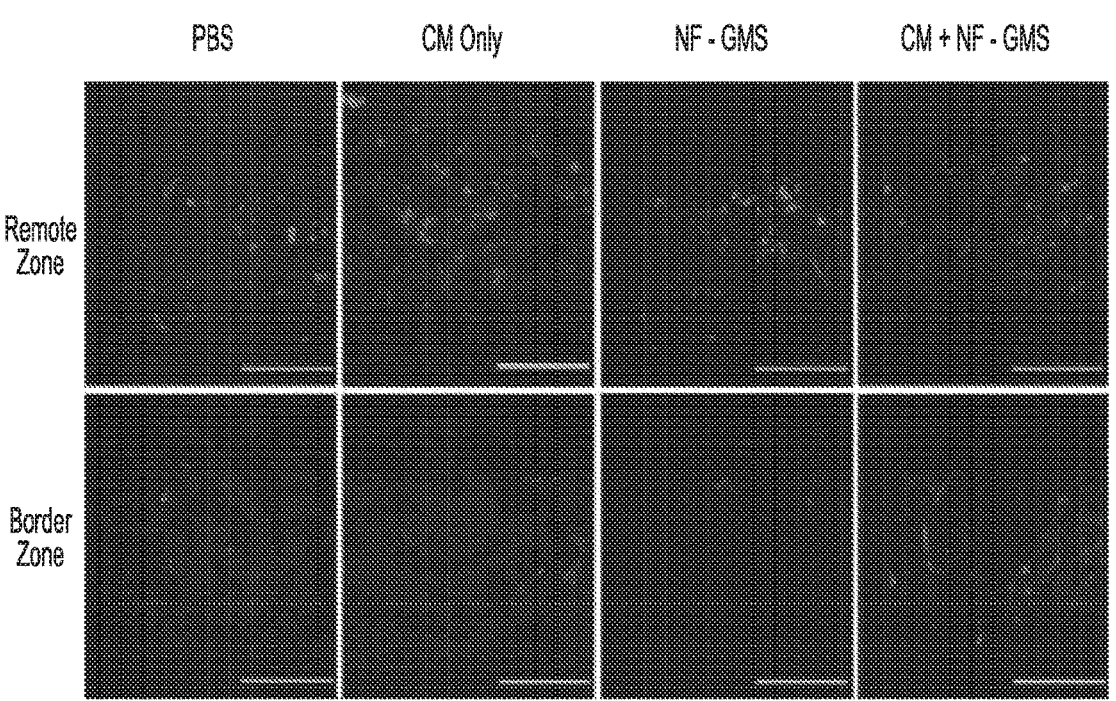
Figure 31A:
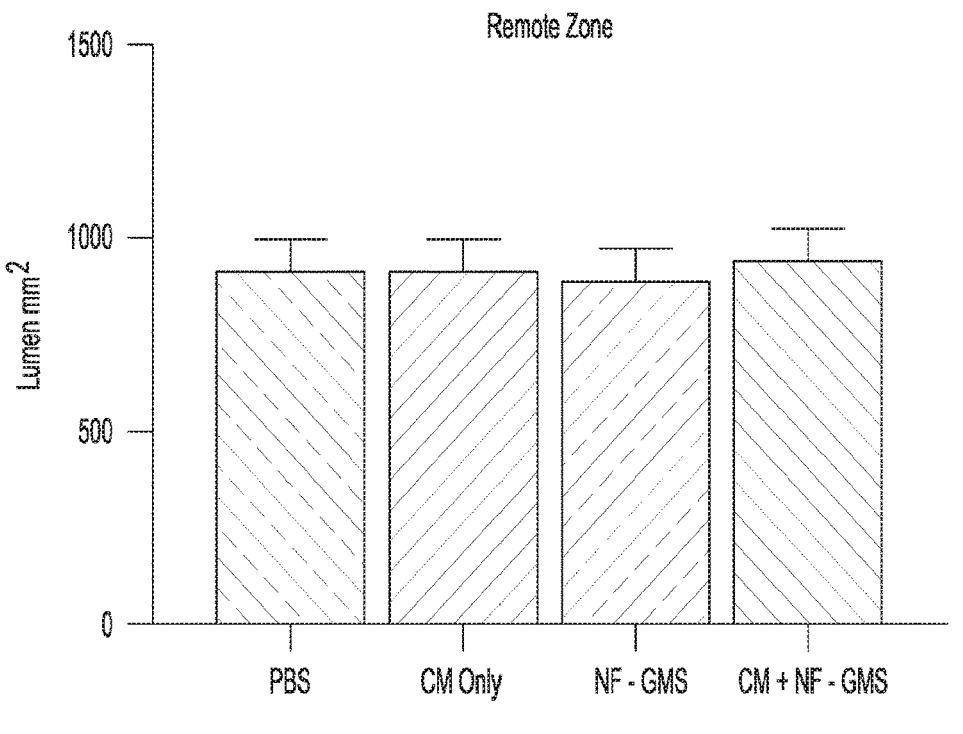
Figures 31B, 32:
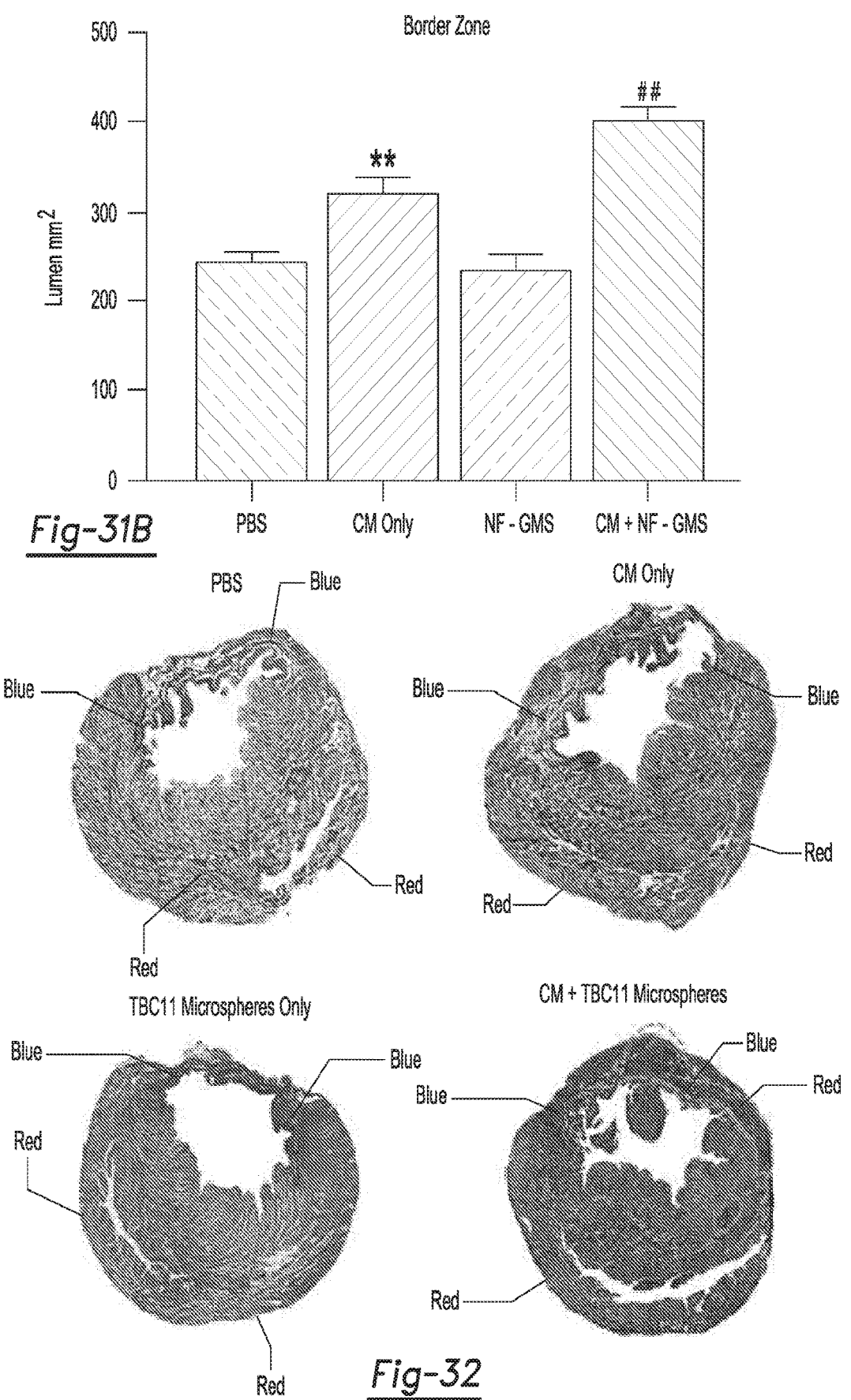
Figures 33, 34A:
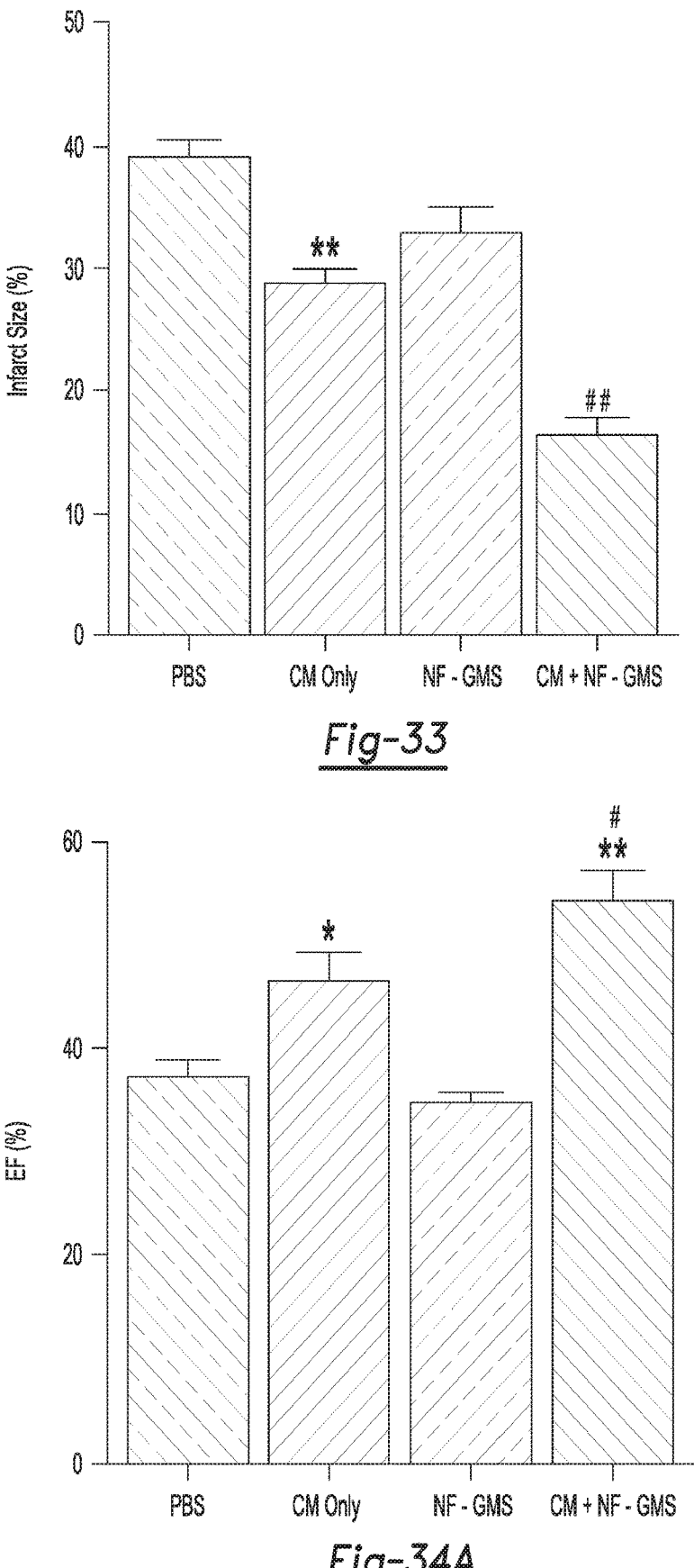
Figure 34B:
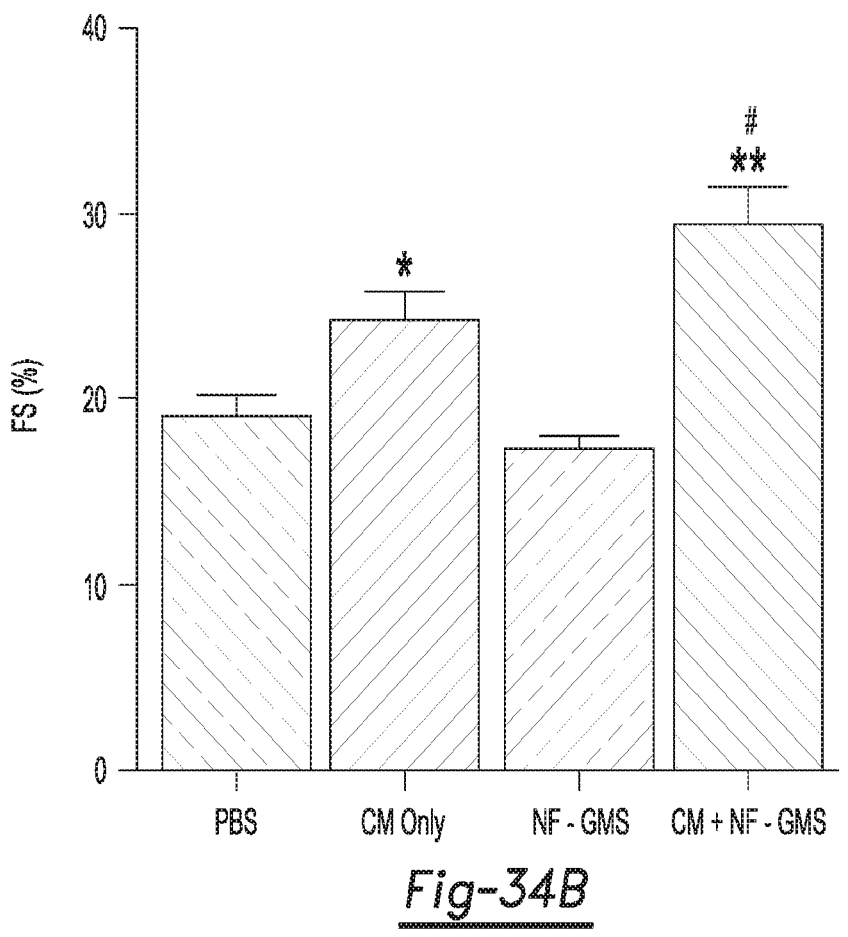
Figure 35:
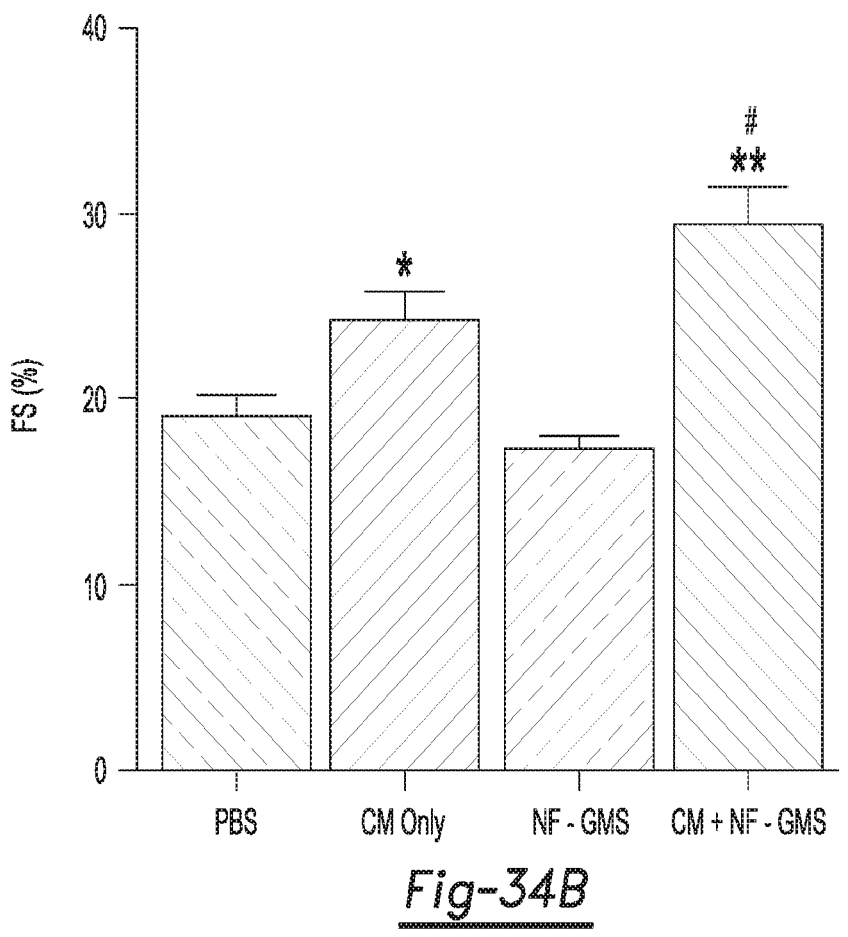

29A-29C), in infarcted rat hearts and illustrating abundant gap junctions between host and transplanted cells (arrows, FIG. 29F) and among transplanted cells were formed as indicated by Connexin 43 staining (FIGS. 29D-29F);

FIG. 30 illustrates black and white reproductions of confocal laser microscope images of vessel-like lumens in a remote zone and a border zone of infarcted rat hearts after 28 days of treatment with PBS ("PBS"), cardiomyocytes only ("CM Only"), TB11 microspheres only ("NF-GMS"), or CMs+TB11 microspheres ("CM+NF-GMS") and stained with the endothelial cell marker CD31, the original red color indicated CD31 positive endothelial cells on the lumen surface of the vessels;

FIGS. 31A and 31B are graphs depicting the quantification of the vessel-like lumens in the remote zone and the border zone of infarcted rat hearts treated with PBS ("PBS"), cardiomyocytes only ("CM Only"), TB11 microspheres only ("NF-GMS"), or CMs+TB11 microspheres ("CM+NF-GMS") (n=9, **, p<0.01, compared with PBS group; ##, p<0.01, compared with CM group);

FIG. 32 illustrates the infarcted rat hearts after 28 days of treatment with PBS ("PBS"), cardiomyocytes only ("CM Only"), TB11 microspheres only ("NF-GMS"), or CMs+TBC11 microspheres ("CM+NF-GMS") using Masson Trichrome staining;

FIG. 33 is a graph of the infarct size (%) for the infarcted rat hearts after 28 days of treatment with PBS ("PBS"), cardiomyocytes only ("CM Only"), TBC11 microspheres only ("NF-GMS"), or CMs+TBC11 microspheres ("CM+NF-GMS");

FIGS. 34A and 34B are graphs, respectively, of the left ventricle ejection fractions (EF, %) and fractional shortening (FS, %) of the infarcted rat hearts after 28 days of treatment with PBS ("PBS"), cardiomyocytes only ("CM Only"), TBC11 microspheres only ("NF-GMS"), or CMs+TBC11 microspheres ("CM+NF-GMS");

FIG. 35 depicts the reaction of a hydrophilic polymer that has the same functional group attached at both ends with a reagent to introduce a different functional group at one of the ends; and FIG. 36 depicts an example of the reactions that take place during the example method 100C in FIG. 2.

DETAILED DESCRIPTION

Many scaffolds have been developed for use in drug delivery and/or tissue regeneration. While scaffolds can have many different characteristics, it may be particularly desirable for a scaffold to be nano-fibrous, injectable, and capable of self-assembly. Nano-fibrous scaffolds may be desirable because they mimic the native extracellular matrix. Injectable scaffolds may be desirable because they can be easily manipulated and involve minimally invasive procedures for a patient. Self-assembling scaffolds may be desirable because they can form macroscopic three-dimensional structures in vivo, and thus can readily fill defects and/or wounds. While each of these particular characteristics may be desirable in a single scaffold, competing characteristics (e.g., polarities) of polymers that achieve a particular characteristic and/or competing requirements involved in scaffold generating processes have made it difficult to generate a scaffold that exhibits all of these characteristics.

A tri-block copolymer is disclosed herein which overcomes these competing requirements. The tri-block copolymer includes three blocks, each of which has a specific functionality and is located in a specific position along the copolymer chain. The tri-block copolymer may be used to generate microspheres that are nano-fibrous, injectable, and able to form a stable hydrogel in vivo. A first of the three blocks is a hydrophobic block, which contributes to the formation of nano-fibers. As such, the microspheres exhibit architectural and structural characteristics that mimic the native extracellular matrix (ECM), and in particular, the ECM fibrillar proteins. A second of the three blocks is a hydrophilic block, which imparts hydrophilicity. The hydrophilicity of the nano-fibrous microspheres enables them to be present in a free-flowing aqueous suspension at room temperature (e.g., from about 18° C. to about 25° C.), which, in turn, enables them to be injected into defects and wounds, including those that are irregularly shaped. Injection is a minimally invasive process. A third of the three blocks is a temperature-responsive block. The temperature-responsive block enables the nano-fibrous microspheres to undergo thermo-responsive reversible hydrophobic interactions (e.g., crosslinking), which results in the self-assembly of a three-dimensional, geometrically stable hydrogel. This gelling property mimics extracellular proteoglycans or polysaccharides. In the examples disclosed herein, it has been found that the ratio of the blocks, the length of the blocks, and the location of the blocks along the chain lead to sufficient polymer chain regularity for nano-fiber formation, retention of a desirable amount of water, and formation of adequate physical crosslinks for hydrogel construction.

As mentioned, the tri-block copolymer and the nano-fibrous microspheres including the tri-block copolymer are thermally-responsive, and can undergo a transition from a more hydrophilic state to a more hydrophobic state or from a soluble state to an insoluble state. During this transition (which may take place after injection in vivo), at least a portion of the tri-block copolymer forms physical crosslinks, resulting in the formation of a hydrogel. The hydrogel can maintain its three-dimensional (3D) geometry in vivo. These characteristics help the hydrogel to remain in its intended location in vivo, which is unlike other injectable scaffolds in free-flowing liquids that are not capable of maintaining their 3D geometry and thus tend to migrate away from the injection site. When the hydrogel stays in its intended location, it can help to retain (in the intended location) any cells and/or other biologically functional molecules that are injected with the nano-fibrous microspheres, and can integrate regenerated tissue with the intended host tissue.

As such, the tri-block copolymer disclosed herein may be particularly suitable for making nano-fibrous microspheres, and the nano-fibrous microspheres may be particularly suitable for tissue engineering. In particular, the examples disclosed herein enable minimally invasive delivery of cells, enhance cell migration and integration, and provide a desirable regenerative environment. The nano-fibrous microspheres may also be used in a variety of other applications, including drug delivery, tissue bulking, adhesives, cosmetics, wound dressing, surgical dressing, and other biomedical applications. Examples of the nano-fibrous microspheres that are temperature responsive in organic solvents may be suitable for use in industrial applications.

Tri-Block Copolymer

Referring now to FIG. 1, an example of the tri-block copolymer 10 includes a first end block 12 consisting of a hydrophobic, nano-fiber forming polymer 12', wherein the first end block 12 is present in the tri-block copolymer 10 at a weight percentage ranging from about 10% to about 89%; a middle block 14 attached to the first end block 12, the middle block 14 consisting of a hydrophilic polymer 14', wherein the middle block 14 is present in the tri-block copolymer 10 at a weight percentage ranging from about 1% to about 89%; and a second end block 16 attached to the middle block 14, the second end block 16 consisting of a temperature-responsive polymer 16', wherein the second end block 16 is present in the tri-block copolymer 10 at a weight percentage ranging from about 1% to about 89%.

The first end block 12 consists of a hydrophobic, nano-fiber forming polymer 12'. Examples the hydrophobic, nano-fiber forming polymer 12' are selected from the group consisting of poly(L-lactic acid) (PLLA), poly(lactide-co-glycolide) (PLGA), polyglycolide, polyanhydrides, poly(ortho ethers), polycaprolactone, poly(hydroxy butyrate), poly(phosphoesters), poly(glycerol sebacate), poly(propylene fumarate), polyphosphazenes, polycarbonates, polyurethanes, non-water-soluble collagen, non-water-soluble gelatin, non-water-soluble elastin, and copolymers thereof.

In the examples disclosed herein, it has been found that the molecular weight, and in particular the number average molecular weight ($M_n$ in g/mol or Daltons), of the hydrophobic, nano-fiber forming polymer 12' has an effect on the ability of the tri-block copolymer 10 to generate nano-fibers. As such, the hydrophobic, nano-fiber forming polymer 12' has a number average molecular weight that is at or above a nano-fiber formation threshold molecular weight. The nano-fiber formation threshold molecular weight may be different for each example of the hydrophobic, nano-fiber forming polymer set forth herein. In one example, the hydrophobic, nano-fiber forming polymer is poly(L-lactic acid) and the number average molecular weight ($M_n$) is at least 5,500 g/mol. In another example, the hydrophobic, nano-fiber forming polymer is poly(lactide-co-glycolide) and the number average molecular weight ($M_n$) is at least 1,000 g/mol.

The middle block 14 consists of a hydrophilic polymer 14'. Examples the hydrophilic polymer 14' are selected from the group consisting of poly(ethylene glycol) (or polyoxyethylene), poly(vinyl alcohol), poly(2-hydroxyethyl methacrylate), polyvinylpyrrolidone, alginate, collagen, gelatin, hyaluronic acid, starch, glycogen, cellulose, carrageenan, dextran, chitin, chitosan, pectin, heparin, heparan sulfate, poly(acrylic acid), poly(acrylamide), poly(N,N'-methylenebisacrylamide), polyvinyl methyl ether, and copolymers thereof.

The hydrophilic block can be easily manipulated to have two different end groups, one of which can attach to the first end block 12 and the other of which can attach to the second end block 16. Modifying the end groups of a water soluble polymer may be desirable to avoid using an organic solvent. This characteristic renders the hydrophilic block particularly desirable for the middle block 14. Moreover, the hydrophilic block contributes to the water-binding ability and the hydrogel formation ability of the tri-block copolymer 10.

The second end block 16 consists of a temperature-responsive polymer 16'. The selection of the temperature-responsive polymer 16' will depend, in part, upon the environment in which it is desirable for the hydrophilic to hydrophobic transition to take place and the liquid carrier used in the suspension to be delivered to that environment. In one example, the temperature-responsive polymer 16' is switchable from the hydrophilic state to the more hydrophobic state in water when exposed to a predetermined temperature; and the temperature-responsive polymer 16' is selected from the group consisting of poly(N-isopropylacrylamide), poly[2-(dimethylamino)ethyl methacrylate], hydroxypropylcellulose, poly(vinylcaprolactame), and polyvinyl methyl ether. In another example, the temperature-responsive polymer 16' is switchable from a soluble state to an insoluble state in an organic solvent when exposed to a predetermined temperature; and the temperature-responsive polymer 16' is selected from the group consisting of polystyrene, polyethylene, polymethylmethacrylate, and polypropylene.

The positioning of the temperature-responsive polymer 16' at the other end of the tri-block copolymer allows the temperature-responsive polymer to be located at the outermost portion of the nano-fibrous gelling microsphere 18 (see FIG. 3) that is formed. Thus, the temperature-responsive polymer 16' in the nano-fibrous gelling microsphere 18 is readily available for crosslinking with other temperature-responsive polymers in other nano-fibrous gelling microspheres 18.

It is to be understood that each of the blocks 12, 14, 16 includes a different type of polymer. As such, if polyvinyl methyl ether is selected as the middle block 14, a different polymer is selected for the second end block 16.

In the examples of the tri-block copolymer 10 disclosed herein, it is to be understood that the blocks 12, 14, 16 are not repeated along the copolymer chain. In some examples, the tri-block copolymer 10 is a linear copolymer, and in other examples, the tri-block copolymer 10 is a branched copolymer. The structure of the chain will depend upon the polymers 12', 14', 16' used in the respective blocks 12, 14, 16.

In the examples disclosed herein, each block 12, 14, 16 represents a certain percentage of the total weight of the copolymer 10. The weight percentages are selected so that the resulting tri-block copolymer 10 is capable of nano-fiber formation, has high hydrophilicity, and is also capable of hydrophobic crosslink formation when exposed to a predetermined temperature. Generally, the tri-block copolymer 10 includes from about 10 wt % to about 89 wt % of the first end block 12; from about 1 wt % to about 89 wt % of the middle block 14; and from about 1 wt % to about 89 wt % of the second end block 16, each of which is with respect to the total weight of the tri-block copolymer 10. In another example, the tri-block copolymer 10 includes from about 30 wt % to about 70 wt % of the first end block 12; from about 3 wt % to about 56 wt % of the middle block 14; and from about 5 wt % to about 65 wt % of the second end block 16, each of which is with respect to the total weight of the tri-block copolymer 10. In still another example, the tri-block copolymer 10 includes from about 50 wt % to about 89 wt % of the first end block 12; from about 5 wt % to about 40 wt % of the middle block 14; and from about 10 wt % to about 45 wt % of the second end block 16, each of which is with respect to the total weight of the tri-block copolymer 10.

In examples of the tri-block copolymer 10, the first end block 12, and thus the hydrophobic, nano-fiber forming polymer 12', is the main component of the tri-block copolymer 10 because it is present in a higher weight percentage than either the middle block 14 or the second end block 16.

The weight percentages will depend upon the particular polymers 12', 14', 16' that are used. In one example, the hydrophobic, nano-fiber forming polymer 12' is poly(L-lactic acid) and at least 68 wt % of the tri-block copolymer 10 is the first end block 12; the hydrophilic polymer 14' is poly(ethylene glycol) and at least 5 wt % of the tri-block copolymer is the middle block 14; and the temperature responsive polymer 16 is poly(N-isopropylacrylamide) and at least 11 wt % of the tri-block copolymer 10 is the second end block 16. The following are more specific examples of the tri-block copolymer 10 with these particular polymers 12', 14', 16': i) the first end block 12 is present in an amount of 68 wt %, the middle block 14 is present in an amount of 9 wt %, and the second end block 16 is present in an amount of 23 wt %; ii) the first end block 12 is present in an amount of 80 wt %, the middle block 14 is present in an amount of 9 wt %, and the second end block 16 is present in an amount of 11 wt %; and iii) the first end block 12 is present in an amount of 84 wt %, the middle block 14 is present in an amount of 5 wt %, and the second end block 16 is present in an amount of 11 wt %.

The tri-block copolymer 10 may be synthesized by any suitable method that will attach the end blocks 12, 16 at opposed ends of the middle block 14. Different example methods are depicted in FIG. 2. Variations of a first example method are shown at reference numerals 100A, 100B, and 100C, and include the processes shown in boxes 104, 106, and 108. Variations of a second example method are shown at reference numerals 102A, 102B, and 102C, and include the processes shown in boxes 104, 110, and 112.

The first example method 100A, 100B, 100C involves synthesizing the hydrophilic polymer 14' and then polymerizing monomers in the presence of the hydrophilic polymer 14' to from the other polymers 12' and 16' attached to the hydrophilic polymer 14'. In an example, the first example method 100A, 100B, 100C includes synthesizing an asymmetrical hydrophilic polymer having two different functional end groups, thereby forming a middle block 14 of a tri-block copolymer 10 (reference numeral 104); polymerizing a hydrophobic monomer using a first of the two different functional end groups, thereby forming a first end block 12 of the tri-block copolymer 10 attached to the middle block 14 (reference numeral 106); and polymerizing a temperature-responsive monomer using a second of the two different functional end groups, thereby forming a second end block 16 of the tri-block copolymer attached to the middle block 14 (reference numeral 108). As designated in FIG. 2 by some of the arrows, the polymerization of the hydrophobic monomer (reference numeral 106) occurs before (in method 100A), simultaneously with (in method 100B), or after (method in 100C) the polymerization of the temperature-responsive monomer (reference numeral 108).

The synthesis of the asymmetrical hydrophilic polymer having two different functional end groups (reference numeral 104) will now be described. In an example, a hydrophilic polymer may be reacted with a reagent that will attach to one end of the hydrophilic polymer. In an example, the ratio of hydrophilic polymer to reagent is 1:1. The hydrophilic polymer may have the same functional group attached at both ends, and the reagent that is reacted with the hydrophilic polymer may introduce a different functional group. An example of this reaction is shown below in FIG. 35, where the hydrophilic polymer is anhydrous poly(ethylene glycol) (where n ranges from about 4 to about 800) and the reagent is 2-bromoisobutyryl bromide.

As depicted by the product in the scheme shown in FIG. 35, this generates an asymmetrical poly(ethylene glycol) polymer with a hydroxyl (—OH) group at one end and a bromine (—Br) functional group at the other end. The reaction shown in FIG. 35 may take place with equimolar amounts of the PEG and the reagent in the presence of tetrahydrofuran (THF) and triethylamine (TEA). In another example, the hydrophilic polymer is poly(2-hydroxyethyl methacrylate) and the reagent is 2-bromoisobutyryl bromide, which generates 2-(2-bromoisobutyryloxy)ethyl methacrylate. The resulting asymmetrical hydrophilic polymer is a bifunctional and orthogonal initiator. The asymmetrical hydrophilic polymer is bifunctional because each of the end functional groups can react, and is orthogonal because the respective reactions at the end functional groups do not interfere with each other. In one example, one of the functional groups (e.g., the hydroxyl group) initiates the ring opening polymerization (ROP) of the hydrophobic monomer, and the other of the functional groups (e.g., the bromine group) initiates the atom transfer radical polymerization (ATRP) of the temperature-responsive monomer. Other functional groups that can initiate ROP include an amine group (—NH$_2$) or a carboxyl group (—COOH). As examples, succinic acid and malonic acid may be used to convert an —OH group of a hydrophilic polymer to a —COOH group; or alanine may be used to convert an —OH group of a hydrophilic polymer to an —NH$_2$ group.

It is to be understood that the asymmetrical hydrophilic polymer may also be a commercially available product (e.g., 2-(2-bromoisobutyryloxy)ethyl methacrylate), and thus the step of synthesizing at reference numeral 104 may not be performed. Rather, the methods 100A, 100B, 100C may involve providing a suitable asymmetrical hydrophilic polymer.

Once the asymmetrical hydrophilic polymer is obtained, any variation of the method 100A, 100B, or 100C may be performed.

In any of these examples, the hydrophobic monomer (used in step 106) may be L-lactide, glycolide, an anhydride monomer, caprolactone, a phosphoester monomer, a phosphazene monomer, a carbonate monomer, or a urethane monomer. Also in any of these examples, the temperature-responsive monomer (used in step 108) may be N-isopropylacrylamide, 2-(dimethylamino)ethyl methacrylate, N-vinylcaprolactame, methyl vinyl ether, styrene, ethylene, methylmethacrylate, or propylene.

In the method 100A, a hydrophobic monomer is polymerized in the presence of the asymmetrical hydrophilic polymer to form the first end block 12 attached to one of the two different functional end groups (reference numeral 106), and then a temperature-responsive monomer is polymerized in the presence of the asymmetrical hydrophilic polymer (having the first end block 12 attached thereto) to form the second end block 16 attached to the other of the two different functional end groups (reference numeral 108). In one example of the method 100A, the asymmetrical poly(ethylene glycol) polymer (from FIG. 35) may be reacted with the hydrophobic monomer, e.g., L-lactide. The asymmetrical PEG polymer acts as the initiator for the ring-opening polymerization of L-lactide, which polymerizes and attaches to the hydroxyl group. This copolymer can then be reacted with the temperature-responsive monomer, e.g., N-isopropylacrylamide. The asymmetrical PEG hydrophilic polymer also acts as the initiator for the atom transfer radical polymerization of N-isopropylacrylamide, which polymerizes and attaches to the bromine group.

In the method 100B, a hydrophobic monomer and a temperature-responsive monomer are simultaneously, but respectively polymerized in the presence of the asymmetrical hydrophilic polymer to form the first end block 12 attached to one of the two different functional end groups (reference numeral 106) and the second end block 16 attached to the other of the two different functional end groups (reference numeral 108).

In the method 100C, a temperature-responsive monomer is polymerized in the presence of the asymmetrical hydrophilic polymer to form the second end block 16 attached to one of the two different functional end groups (reference numeral 108), and then a hydrophobic monomer is polymerized in the presence of the asymmetrical hydrophilic polymer (having the second end block 12 attached thereto) to form the first end block 12 attached to the other of the two different functional end groups (reference numeral 106). One example of the method 100C is shown in FIG. 36.

In FIG. 36, the asymmetrical poly(ethylene glycol) polymer (from FIG. 35) is first reacted with the temperature-responsive monomer, e.g., N-isopropylacrylamide, to form a hydroxyl-terminated di-block copolymer (labeled 1 in FIG. 36), and then the hydroxyl-terminated di-block copolymer 1 is reacted with the hydrophobic monomer, e.g., L-lactide, to form an example of the tri-block copolymer 10 disclosed herein (labeled 2 in FIG. 36). The ATRP of the N-isopropylacrylamide monomer is initiated by the bromine group of the asymmetrical poly(ethylene glycol) polymer (from FIG. 35), which form the di-block copolymer 1. This reaction may take place in a water/ethanol mixture with copper chloride (CuCl) and tris-[2-(dimethylamino)ethyl]amine (Me6). The ROP of L-lactide is initiated by the hydroxyl end group of the di-block copolymer 1 to form an example of the tri-block copolymer (labeled copolymer 2 in FIG. 36), This reaction may be performed in tetrahydrofuran (THF) with stannous 2-ethlhexanoate (Sn(Oct)$_2$) at about 80° C.

In any of the example methods 100A, 100B, 100C, a sufficient amount of the hydrophobic monomer is polymerized to form the first end block 12 with a number average molecular weight at or above the nano-fiber formation threshold molecular weight.

The second example method 102A, 102B, 102C shown in FIG. 2 involves synthesizing the hydrophilic polymer 14' and then conjugating the other polymers 12' and 16' to opposed ends of the hydrophilic polymer 14'. In an example, the second example method 102A, 102B, 102C includes synthesizing an asymmetrical hydrophilic polymer having two different functional end groups, thereby forming a middle block 14 of a tri-block copolymer 10 (reference numeral 104); conjugating a first end block 12 to the middle block 14 through a first of the two different functional end groups, the first end block including a hydrophobic, nano-fiber forming polymer 12' (reference numeral 110); and conjugating a second end block 16 to the middle block 14 through a second of the two different functional end groups, the second end block 16 including a temperature-responsive polymer 16' (reference numeral 112). As designated in FIG. 2 by some of the arrows, the conjugation of the first end block 14 (reference numeral 110) occurs before (in method 102A), simultaneously with (in method 102B), or after (method in 102C) the conjugation of the second end block 16 (reference numeral 108).

In the methods 102A, 102B, and 102C, the synthesis of the asymmetrical hydrophilic polymer having two different functional end groups (reference numeral 104) may be performed as described herein. Once the asymmetrical hydrophilic polymer is obtained, any variation of the method 102A, 102B, or 102C may be performed.

In the method 102A, a hydrophobic, nano-fiber forming polymer 12' is conjugated to the asymmetrical hydrophilic polymer through one of the two different functional end groups (reference numeral 110), and then a temperature-responsive polymer 16' is conjugated to the asymmetrical hydrophilic polymer (having the first end block 12 attached thereto) to form the second end block 16 attached to the other of the two different functional end groups (reference numeral 112). In one example of the method 100A, the asymmetrical poly(ethylene glycol) polymer (from FIG. 35) may be conjugated to the hydrophobic polymer, e.g., poly (L-lactic acid). This copolymer can then be reacted with the temperature-responsive polymer, e.g., poly(N-isopropylacrylamide).

In the method 102B, a hydrophobic, nano-fiber forming polymer 12' and a temperature-responsive polymer 16' are simultaneously and respectively conjugated to the asymmetrical hydrophilic polymer to form the first end block 12 attached to one of the two different functional end groups (reference numeral 110) and the second end block 16 attached to the other of the two different functional end groups (reference numeral 112).

In the method 102C, a temperature-responsive polymer 16' is conjugated to the asymmetrical hydrophilic polymer to form the second end block 16 attached to one of the two different functional end groups (reference numeral 112), and then a hydrophobic, nano-fiber forming polymer 12' is conjugated to the asymmetrical hydrophilic polymer (having the second end block 12 attached thereto) to form the first end block 12 attached to the other of the two different functional end groups (reference numeral 110).

In any of the example methods 102A, 102B, 102C, the hydrophobic, nano-fiber forming polymer 12' is synthesized prior to the formation of the tri-block copolymer 10. Any of the example methods 102A, 102B, 102C may further include polymerizing a hydrophobic monomer to form the hydrophobic, nano-fiber forming polymer 12' and/or polymerizing the temperature-responsive monomer to form the temperature-responsive polymer 16'. In one specific example, the method 102A, 102B, or 102C includes polymerizing a sufficient amount of a hydrophobic monomer to form the hydrophobic, nano-fiber forming polymer 12' with a number average molecular weight at or above a nano-fiber formation threshold molecular weight.

Nano-Fibrous Gelling Microspheres

The tri-block copolymer 10 may be used to form nano-fibrous gelling microspheres. An example of the nano-fibrous gelling microsphere includes: interconnected nano-fibers of a tri-block copolymer 10 (including a first end block 12 of a hydrophobic, nano-fiber forming polymer 12', wherein the first end block 12 is present in the tri-block copolymer 10 at a weight percentage ranging from about 10% to about 89%, a middle block 14 attached to the first end block 12, the middle block 14 consisting of a hydrophilic polymer 14', wherein the middle block 14 is present in the tri-block copolymer 10 at a weight percentage ranging from about 1% to about 89%, and a second end block 16 attached to the middle block 14, the second end block 16 consisting of a temperature-responsive polymer 16', wherein the second end block 16 is present in the tri-block copolymer 10 at a weight percentage ranging from about 1% to about 89%); and spaces formed between the interconnected nano-fibers, wherein the nano-fibrous gelling microsphere is suspendable in a liquid at a first temperature and is to form a hydrogel in the liquid at a second temperature that is higher than the first temperature.

Figures 3A, 3B, 4:
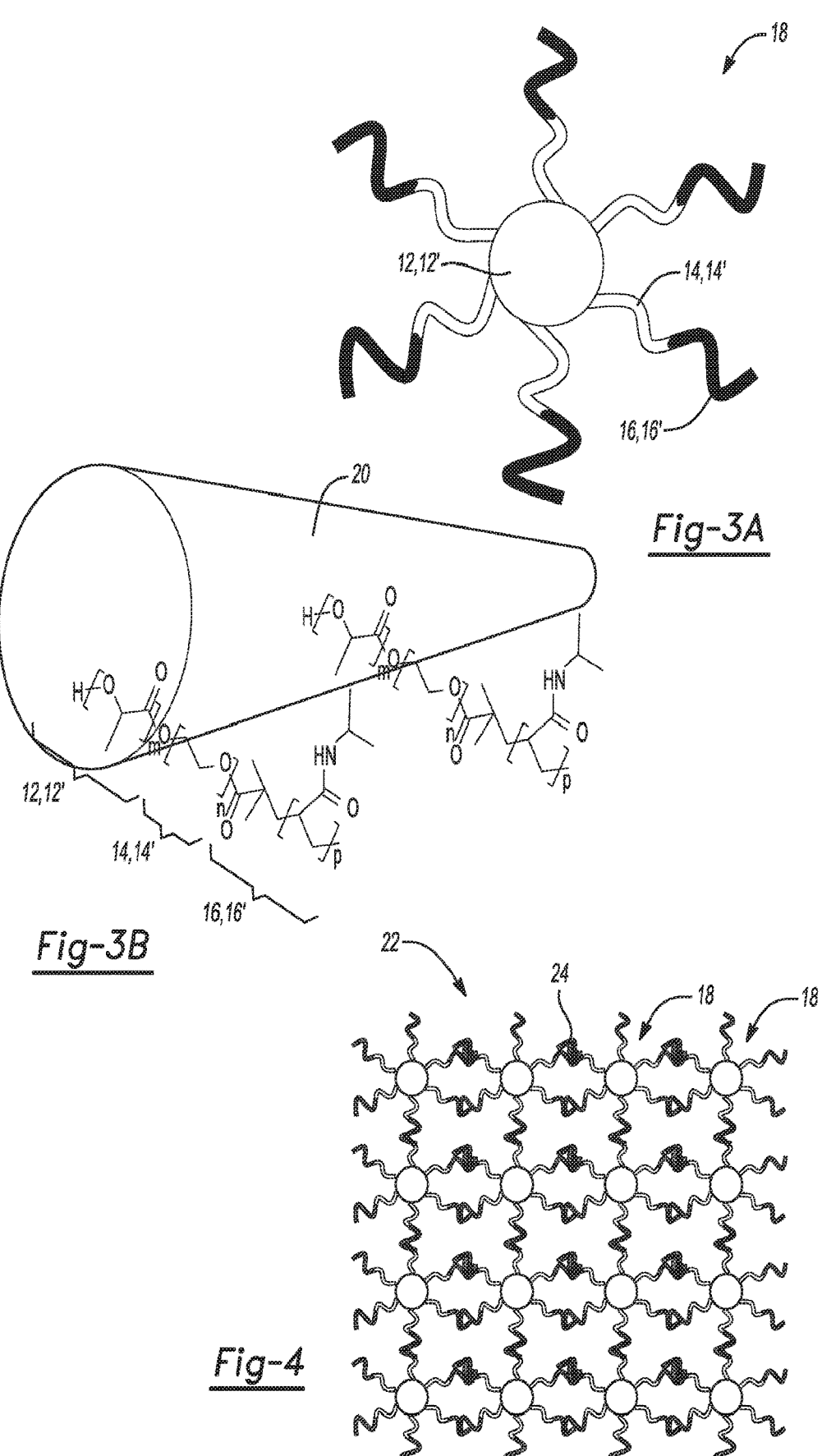
FIG. 3A is a schematic illustration of a nano-fibrous gelling microsphere.
FIG. 3B is a schematic perspective view of a nano-fiber of the nano-fibrous gelling microsphere.
FIG. 4 is a schematic illustration of an example hydrogel that is formed when the nano-fibrous gelling microspheres are exposed to a predetermined temperature.

An example of the nano-fibrous gelling microsphere 18 is shown in FIG. 3A, and an example of one nano-fiber 20 is shown schematically in FIG. 3B. The nano-fibers 20 of the nano-fibrous gelling microspheres 18 may have a core-corona type of structure, where the first end block 12 (including the hydrophobic, nano-fiber forming polymer 12') forms the fiber (the core), and the middle block 14 (including the hydrophilic polymer 14') and the second end block 16 form the outermost layer of the fiber (the corona).

Each nano-fiber 20 has a diameter ranging from about 1 nm to about 1000 nm. The length of the nano-fibers 20 may be on the nano-scale or may be larger. The spaces between the nano-fibers 20 may be less than 2 µm in diameter.

The entire structure of the nano-fibrous gelling microsphere 18 has a diameter D ranging from about 5 µm to about 1000 µm.

Some examples of the nano-fibrous gelling microsphere 18 may be single level porous structures, where the spaces between the nano-fibers 20 are the only pores of the microspheres 18. In other words, these examples of the nano-fibrous gelling microsphere 18 do not include any other larger openings. Other examples of the nano-fibrous gelling microsphere 18 may be multi-level porous structures with at least one opening larger than the spaces between the nano-fibers 20. In one example, the nano-fibrous gelling microsphere 18 includes a single hollow core surrounded by a shell made up of the nano-fibers 20. In another example, the nano-fibrous gelling microsphere 18 includes regular spherical macro-scale pores (ranging from about 100 µm to about 500 µm in diameter), micro-scale interpore openings (i.e., openings that connect one macro-scale pore to another macro-scale pore) of about 100 µm, and spaces (less than 5 µm in diameter) between the nano-fibers 20.

To form the nano-fibrous gelling microspheres 18, the tri-block copolymer 10 may be exposed to a series of self-assembling processes. One example method includes causing the tri-block copolymer 10 to self-assemble into nano-fibrous gelling microspheres 18 by dissolving the tri-block copolymer to form a solution; emulsifying the solution to form liquid microspheres; and inducing phase separation of the liquid microspheres.

In this example, the tri-block copolymer 10 is first dissolved in a suitable solvent to form a copolymer solution. Examples of the solvent include tetrahydrofuran (THF), dimethyl formamide (DMF), pyridine, a THF-methanol mixture, a dioxane-methanol mixture, a dioxane-water mixture, a dioxane-acetone mixture, or a dioxane-pyridine mixture. The solvent may vary depending upon the blocks 12, 14, 16 of the tri-block copolymer 10. In one example, the tri-block copolymer 10 may be dissolved in the solvent at a concentration ranging from about 0.5% (w/v) to about 15% (w/v). In another example, the tri-block copolymer 10 may be dissolved in the solvent at a concentration ranging from about 1% (w/v) to about 5% (w/v). In an example, the tri-block copolymer 10 is dissolved in the solvent at a concentration of about 2% (w/v).

The copolymer solution is then emulsified into liquid microspheres. In an example, glycerol is quickly added to the copolymer solution. As the glycerol is added, the mixture is stirred (e.g., using a magnetic stir bar or a mechanical stirrer). In another example, the copolymer solution is added to glycerol. As the copolymer solution is added, the mixture is stirred. The temperature of the mixture may range from about 20° C. to about 100° C. In an example, the temperature of the mixture may be maintained at about 50° C. The copolymer solution is rapidly (e.g., within a few seconds) emulsified into copolymer solution droplets, but there is no phase inversion.

Phase separation is then induced in order to form the nano-fibrous structure. Phase separation may be induced by pouring the copolymer emulsion into liquid nitrogen. Phase separation is a thermodynamic process, in which a homogeneous multi-component system tends to self-assemble into multiple phases to lower system free energy. For copolymer solutions, copolymer-rich and copolymer-lean phases will form during the self-assembly, with the former solidifying into a copolymer skeleton and the latter becoming the void space during solvent extraction. As such, phase separation forms a copolymer skeleton of the microsphere, as well as a liquid phase that includes glycerol and the solvent. The glycerol and the solvent are extracted from the copolymer skeleton (e.g., by washing with water), and microspheres are formed. The type of copolymer and solvent, as well as the solution concentration and solvent extraction processes, all play a role in the structure formation during phase separation. As illustrated in the example section, certain copolymers will form nanofibers, and other copolymers will aggregate together.

The microspheres that are formed may be freeze-dried.

Use of the Nano-Fibrous Gelling Microspheres

The nano-fibrous gelling microspheres 18 disclosed herein may be particularly suitable for in vivo biomedical applications, such as tissue engineering, drug delivery, etc.

The nano-fibrous gelling microspheres 18 may be suspended in a liquid carrier having a temperature that is below body temperature (below 36° C.). In some examples, the liquid carrier, and thus the suspension, is at a temperature ranging from about 18° C. to about 35° C., or from about 18° C. to about 25° C. When the suspension is maintained below body temperature, the microspheres 18 maintain their nano-fibrous structure. When in suspension, the nano-fibrous gelling microspheres 18 can be readily injected subcutaneously.

The liquid carrier used may depend upon the temperature-responsive polymer 16' in the second end block 16 of the tri-block copolymer 10, and may also depend upon the environment into which the suspension is to be injected. When the temperature-responsive polymer 16' is thermo-responsive in water, the liquid carrier may be water alone, or a water (aqueous) based solution including an organic or inorganic solute, a buffer, a tissue culture medium, or a bodily fluid. Examples of organic or inorganic solutes include salts (e.g., sodium chloride, calcium chloride, calcium phosphate, calcium sulfate, etc.), sugars, polysaccharides, peptides, proteins, ribonucleic acids (RNA), deoxyribonucleic acids (DNA), etc. One example of a buffer solution is phosphate buffered saline. When the temperature-responsive polymer 16' is thermo-responsive in an organic solvent, the liquid carrier may be the organic solvent alone, or an organic-based solution including water, a buffer, a tissue culture medium, or a body fluid.

In some examples, the suspension may include the liquid carrier, the plurality of nano-fibrous gelling microspheres 18, and a plurality of cells or biologically functional molecules attached to at least some of the plurality of the nano-fibrous gelling microspheres 18 or mixed in the liquid carrier with the plurality of the nano-fibrous gelling microspheres 18. In an example, the suspension includes a number ratio of nano-fibrous gelling microspheres 18 to cells ranging from about 1:1 to about 1:1000. Any cells or biologically functional molecules may be attached to the nano-fibrous gelling microspheres 18 or mixed in the liquid carrier. Example cells include tissue-specific cells, such as cardiomyocytes, smooth muscle cells, skeletal muscle cells, endothelial cells, osteoblasts, chondrocytes, nucleus pulposus cells, fibroblasts, hepatocytes, neurons, blood cells, immune cells, germ cells, etc., and their progenitor cells, adult stem cells, embryonic stem cells, induced pluripotent stem cells, etc. Examples of suitable biologically functional molecules include chemokine ligand 2, chemokine ligand 7, interleukin 4, interleukin 13, transforming growth factor-beta (TGF-β), fibroblast growth factor (FGF), VEGF, platelet derived growth factor (PDGF), parathyroid hormone (PTH), chemoattractant, bone morphogenetic protein (BMP), derivatives thereof, and combinations thereof.

When the cells or biologically functional molecules are attached to the nano-fibrous gelling microspheres 18, any suitable seeding method may be used. Seeding methods may involve dripping, mixing, chemically reacting, physically attaching, etc.

When the cells or biologically functional molecules are mixed in the liquid carrier, they remain unattached from the nano-fibrous gelling microspheres 18, and can be at least partially encapsulated by the hydrogel that is formed when the nano-fibrous gelling microspheres 18 are exposed to a temperature to which the tri-block copolymer 10 is thermally responsive.

A treatment method utilizing the nano-fibrous gelling microspheres 18 may include introducing the nano-fibrous gelling microspheres 18 into an aqueous solution at a temperature that is below a body temperature, thereby forming a suspension; and injecting the suspension into a heart, bone, smooth muscle, blood vessel, heart valve, cardiac muscle, skeletal muscle, bladder, tendon, ligament, skin, fat, cartilage, intervertebral disc, breast, liver, intestine, esophagus, trachea, lung, or nerve. Any example of the nano-fibrous gelling microspheres 18 and liquid carrier may be used, and in some instances, the cells and/or biologically functional molecules may also be included in the suspension that is injected. When the temperature-responsive block 16 is responsive in an organic solvent, the aqueous solution may be replaced with a suitable organic solvent.

One specific example treatment method is for regenerating an infarcted heart. This example method includes introducing the nano-fibrous gelling microspheres 18 into a buffer solution at a temperature that is below a body temperature, thereby forming a suspension, wherein the plurality of cells includes cardiomyocytes; and injecting the suspension into the infarcted heart.

The suspension may be injected subcutaneously into the desired area. The injection may be performed using a syringe or another suitable tool.

Once injected, the suspension is exposed to the body temperature, which generally ranges from about 36.5° C. to about 37.5° C., but, in some instances may be higher. The increased temperature causes the temperature-responsive blocks 16 of the nano-fibrous gelling microspheres 18 to undergo a hydrophilic to hydrophobic transition to form physical crosslinks. These crosslinks are shown at reference numeral 24 in FIG. 4, which depicts several nano-fibrous gelling microspheres 18 crosslinked together. The hydrophilic to hydrophobic transition and resulting crosslinks 24 form the hydrogel 22. As shown schematically in FIG. 4, the individual nano-fibrous gelling microspheres 18 maintain their microscopic 3D geometry, as well as their nano-fibrous architecture.

To further illustrate the present disclosure, examples are given herein. It is to be understood that these examples are provided for illustrative purposes and are not to be construed as limiting the scope of the present disclosure.

EXAMPLES

Example 1

Synthesis of Tri-Block copolymer

The asymmetrical hydrophilic polymer (AHP), Br-PEG-OH, was synthesized using the reaction of bromoisobutyryl bromide (BIBB) with an equimolar amount of anhydrous HO-PEG-OH in the presence of tetrahydrofuran (THF) and triethylamine (Et₃N). More specifically, dry tetrahydrofuran (THF) (25 mL), dry polyethylene glycol (PEG) (6.68 mmol) and dry triethylamine (TEA) (20 mmol, 1.5 mL) were placed in a 250 mL round-bottom flask, and kept under a nitrogen atmosphere. Within 1 hour, bromoisobutyryl bromide (BIBB) (6.68 mmol, 0.83 ml) was slowly added via a dropping funnel. After the addition was complete, the mixture was stirred at room temperature overnight. The precipitated salts were filtered off, and the filtrate was evaporated in vacuum. Then, 1 M hydrochloric acid (HCl) (30 mL) was added and the mixture was extracted with dichloromethane (3×20 mL). The combined organic layers were washed three times with water (50 mL) to remove salt. The organic layer was dried over anhydrous $Na_2SO_4$ overnight. After removal of the solvent, the polymer was precipitated into cold ethyl ether and collected by filtration. The resultant white powder was dried in vacuum for 24 hours to give HO-PEG-Br.

A hydroxyl-terminated di-block copolymer (HO-PEG-PNIPAm) was prepared by reacting Br-PEG-OH with N-iso-propylacrylamide. The bromine end group of Br-PEG-OH initiated the atom transfer radical polymerization of the N-isopropylacrylamide monomer. The PEG macroinitiator (Br-PEG-OH, $M_n$=1551) (0.6 mmol, 1 g), NIPAm (26.5 mmol, 3 g), and CuCl (0.170 mmol, 0.016.8 g) were placed in a 250 mL round-bottom flask under nitrogen protection and sealed with rubber septum stoppers. Milli-Q water (20 mL) and $Me_6TREN$ (0.174 mmol, 0.04 g) were placed in a Schlenk tube and purged with $N_2$ gas for about 40 minutes. The solution was transferred to the round-bottom flask using a syringe under nitrogen protection. The reaction mixture was then stirred under nitrogen atmosphere for about 24 hours. The reaction was then stopped by opening the vessel to air. The reaction mixture was precipitated into ethyl ether, filtered, and dried. The resulting solid was then dissolved in $H_2O$ and dialyzed (MW cut-off 3.5 kDa) against de-ionized water for 3 days to remove unreacted PEG-macroinitiator. The mixture was then lyophilized for three days to give the HO-PEG-PNIPAm di-block copolymer.

A PLLA-PEG-PNIPAm tri-block copolymer was prepared by reacting the hydroxyl-terminated di-block copolymer (HO-PEG-PNIPAm) with L-lactide in tetrahydrofuran. More specifically, dry THF (10 mL), L-lactide (139 mmol, 2 g), HO-PEG-PNIPAm (Mn=5371) (0.0559 mmol, 0.3 g) and $Sn(Oct)_2$ (0.4 mmol, 0.162 g) were mixed in a 50 mL round-bottom flask with stirring and nitrogen purging. The mixture was heated to 80° C. under nitrogen protection for complete melting. The polymerization was carried out at 80° C. under nitrogen protection for about 24 hours. The crude product was dissolved in 20 mL chloroform, precipitated in 100 mL cold methanol, and then vacuum dried.

The resulting tri-block copolymer (PLLA-PEG-PNIPAm) was characterized using and $^1$H NMR (nuclear magnetic resonance) and FTIR (Fourier-transform infrared spectroscopy). The $^1$H NMR spectrum of the copolymer was recorded with an Inova 400 NMR instrument operating at 400 MHz at room temperature using $CDCl_3$ as the solvent.

Figures 5, 6:
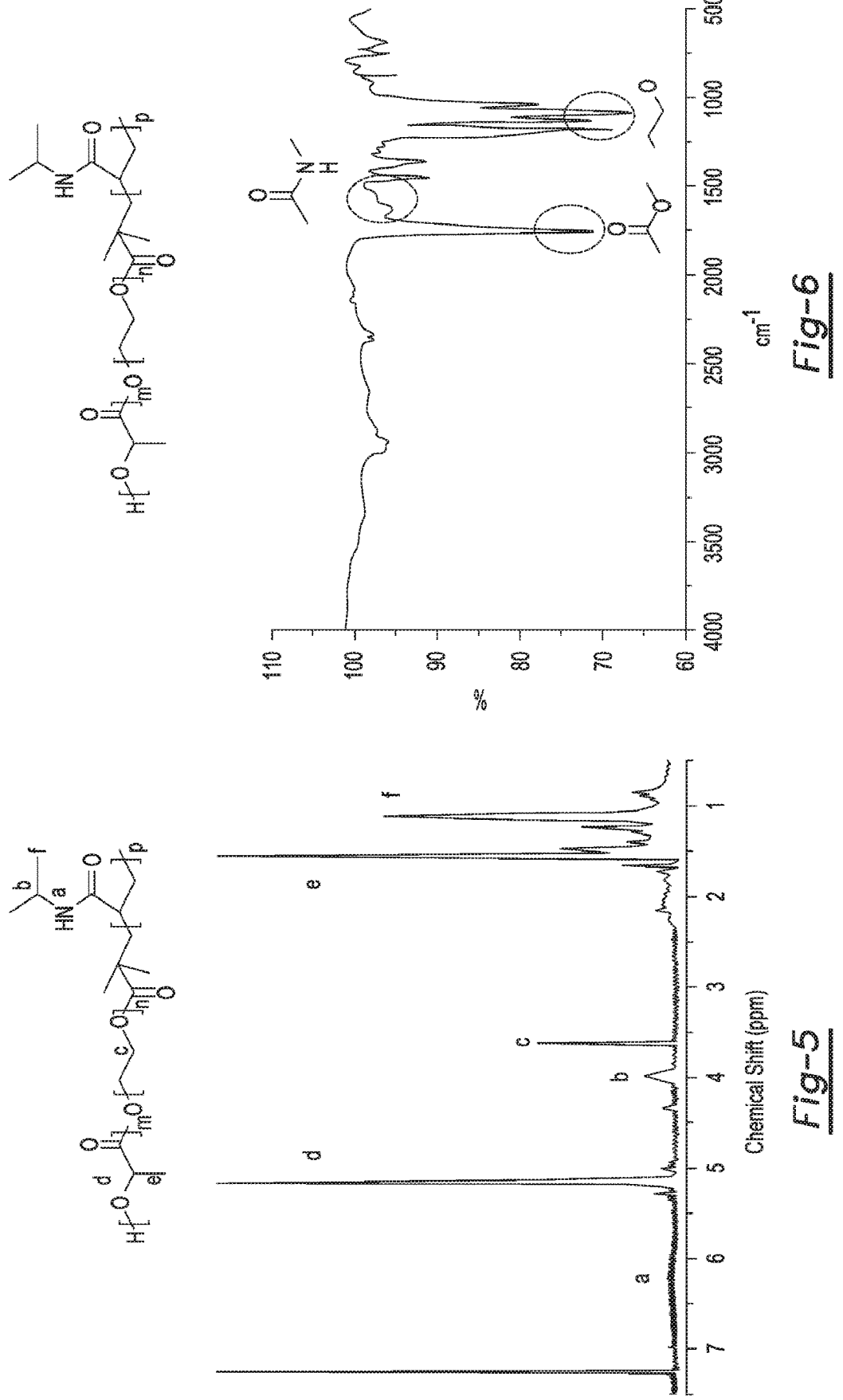
FIG. 5 is an $^1$H NMR spectrum for an example of the tri-block copolymer disclosed herein.
FIG. 6 is an FTIR spectrum for an example of the tri-block copolymer disclosed herein.

The $^1$H NMR results for PLLA-PEG-PNIPAm are shown in FIG. 5. The resonance bands observed in the regions of 5.2 ppm (d) and 1.6 ppm (e) are attributed to methine protons in the backbone and the pendent methyl protons of PLLA, respectively. The band at 3.6 ppm (c) is attributed to methylene protons of PEG. The bands at 1.2 ppm (f), 4.0 ppm (b) and 6.4 ppm (a) are attributed to methyl protons, pendent methine protons and amine protons of PNIPAm, respectively.

The FTIR results for PLLA-PEG-PNIPAm are shown in FIG. 6. The stretching vibration of the C=O (ester) groups of PLLA block appeared at 1750 cm$^{-1}$, the stretching vibration of the C—O groups of PEG block appeared at 1000-1250 cm$^{-1}$, and the stretching vibration of the C=O (amide) groups of PNIPAm block appeared at 1650 cm$^{-1}$.

Both the $^1$H NMR and the FTIR results confirmed that the tri-block copolymer was successfully synthesized.

Thermally Induced Phase Transition Behavior of Di-Block and Tri-Block Copolymers Dynamic light scattering (DLS) was used to monitor the lower critical solution temperature (LCST) of the hydroxyl-terminated di-block copolymer (HO-PEG-PNIPAm) and the tri-block copolymer having a weight percent of PLLA:PEG:PNIPAm at 68:9:23 in water. 0.1 wt % of the bi-block PEG-PNIPAm copolymer was present in one aqueous solution, and 0.01 wt % of the tri-block PLLA-PEG-PNIPAm copolymer was present in another aqueous solution. The hydrodynamic diameter (Dh) of the di-block and tri-block copolymers was evaluated using a Zetasizer Nano ZS dynamic light scattering (DLS) instrument (Malvern, UK). A wavelength of 633 nm and a scattering angle of 173° were fixed. The dispersant refractive index and the viscosity of water were set to be 1.330 and 0.8872 cP, respectively. The measurements were performed from at temperatures from 25° C. to 50° C.

Figure 7B:
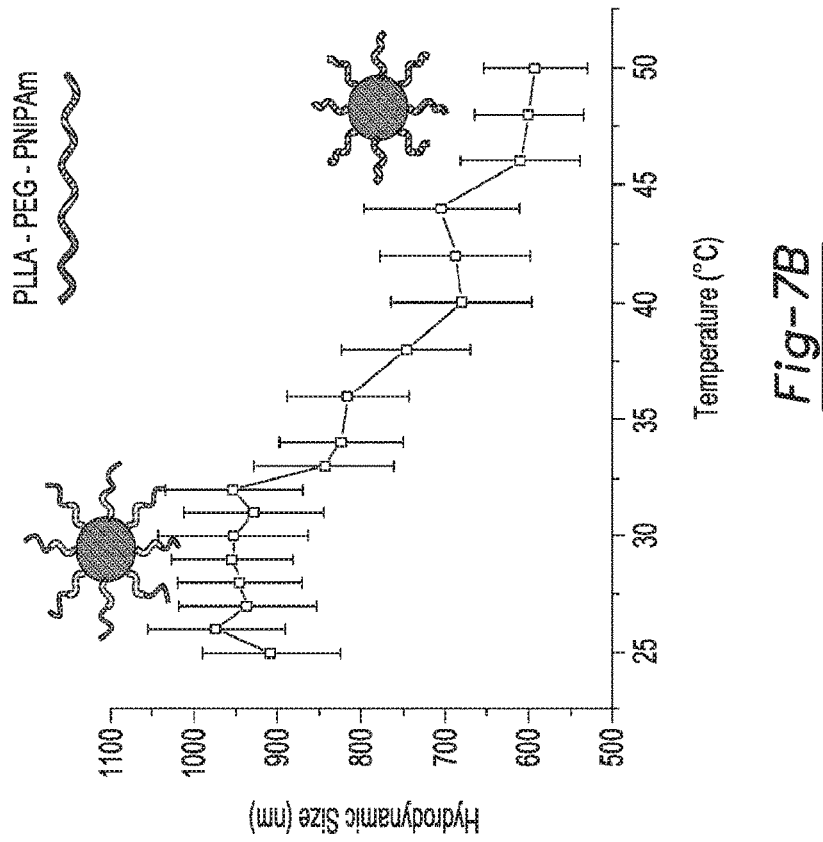
FIGS. 7A and 7B are graphs depicting the hydrodynamic size (nm, Y-axis) versus the temperature (° C., X-axis) for a di-block copolymer and an example of the tri-block copolymer disclosed herein, and also schematically depicting the structure of the respective copolymer below and above the lower critical solution temperature (LCST)
Figure 7A:
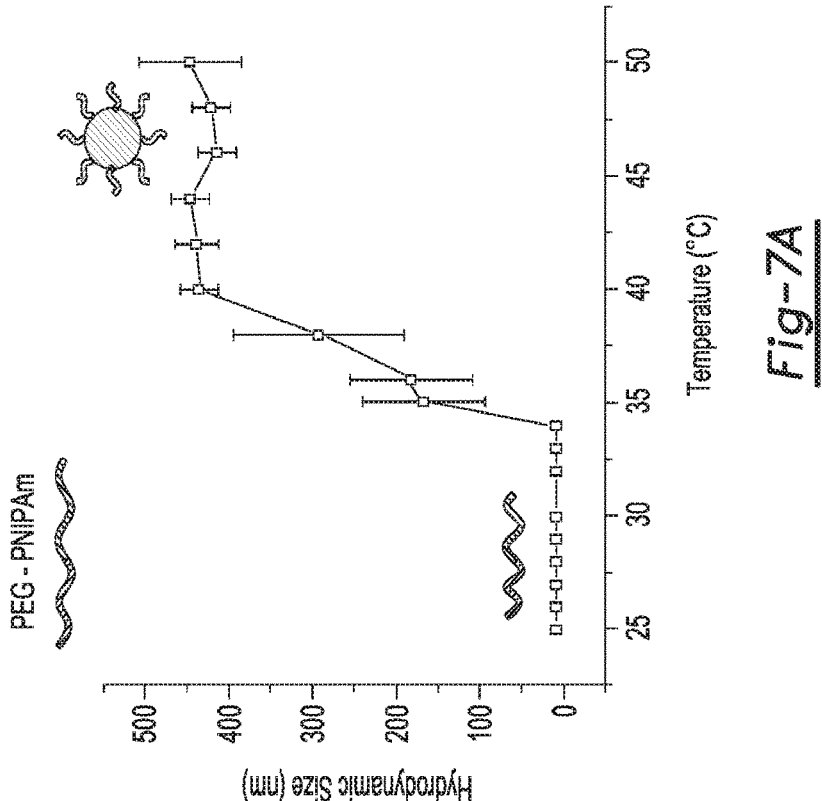

As shown in FIG. 7A, the hydroxyl-terminated di-block copolymer (HO-PEG-PNIPAm) copolymer formed micelles above the LCST of the linear PNIPAm chain, which is around 32° C. to 34° C. The data in FIG. 7A indicates that the di-block copolymer was well dissolved in water with an average hydrodynamic diameter (Dh) of about 10 nm at temperatures below 34° C. By increasing the temperature, the stretched PNIPAm chains collapsed, and the water-soluble PEG blocks were extended to the outer surface. Core-shell micelles were formed, as illustrated schematically in the graph of FIG. 7A. Dh became a constant above the transition temperature region, indicating that the PNIPAm block was fully collapsed and the LCST of HO-PEG-PNIPAm di-block copolymer was approximately 34° C.

The data in FIG. 7B indicates that the PLLA-PEG-PNIPAm (68:9:23) tri-block copolymer formed micelles at all temperatures with PLLA block in the core and PEG-PNIPAm blocks in the shell. The Dh of the polymeric micelles remained constant at about 950 nm at temperatures below 32° C. By increasing the temperature, the stretched PNIPAm chains collapsed, and the Dh of the polymeric micelles shrank to 600 nm. As indicated by the sudden change in the particle size caused by conformational transition, the LCST of PLLA-PEG-PNIPAm tri-block copolymer was determined to be about 32° C.

Example 2

Synthesis of Tri-Block Copolymers

Different examples of the tri-block copolymer were prepared with poly(L-lactic acid) (PLLA), polyethylene glycol (PEG), and poly(N-isopropylacrylamide) (PNIPAm). Varying copolymers were synthesized using different asymmetrical hydrophilic polymers and/or feed mass ratios, and/or reaction times.

The different asymmetrical hydrophilic polymers were based on polyethylene glycol (PEG) of different molecular weights. The PEG polymer was reacted with 2-bromoisobutyryl bromide as shown in FIG. 35 and described in Example 1. The resulting asymmetrical hydrophilic polymers included a hydroxyl end group and a bromine end group. Table 1 shows the various example asymmetrical hydrophilic polymers (AHP) and their corresponding number average molecular weight ($M_n$, g/mol), weight average molecular weight ($M_w$, g/mol), and ratio of $M_w/M_n$. Both molecular weights were determined using gel permeation chromatography (GPC), specifically a Waters gel permeation chromatograph model 440. THF was used as the eluent, at a flow rate of 1.0 mL/minute. The molecular weights and polydispersity were calibrated with polystyrene standards.

TABLE 1

| AHP Identifier | Composition | $M_n$ | $M_w$ | $M_w/M_n$ |
|---|---|---|---|---|
| AHP1 | HO-PEG$_{1000}$-Br | 810 | 907 | 1.12 |
| AHP2 | HO-PEG$_{2000}$-Br | 1551 | 1722 | 1.11 |
| AHP3 | HO-PEG$_{4000}$-Br | 2753 | 3221 | 1.17 |

The AHPs were reacted with N-isopropylacrylamide (NI-PAm) at different feed ratios and/or reaction times to generate several different di-block copolymers. The first reaction in FIG. 36 is representative of this reaction, where the bromine functional group of the asymmetrical hydrophilic polymer initiates the atom transfer radical polymerization of the N-isopropylacrylamide. These reactions were performed as described in Example 1. The resulting di-block copolymers included a hydroxyl end group, the PEG hydrophilic polymer as a middle block, and poly(N-isopropylacrylamide) (PNIPAm) as an end block. Table 2 shows the various example di-block copolymers and their corresponding $M_n$, $M_w$, and ratio of $M_w/M_n$ (determined as described herein). Table 2 also shows the asymmetrical hydrophilic polymer used in the reaction, the feed mass ratio of the NIPAm to the AHP, and the reaction time.

TABLE 2

| Di-Block Copolymer Identifier | Composition | AHP used | Feed Mass Ratio (NIPAm:AHP) | Reaction Time (hours) | $M_n$ | $M_W$ | $M_W/M_n$ |
|---|---|---|---|---|---|---|---|
| DBC1 | HO-PEG$_{1000}$-PNIPAm | AHP1 | 10:1 | 24 | 1302 | 1588 | 1.22 |
| DBC2 | HO-PEG$_{1000}$-PNIPAm | AHP1 | 10:1 | 48 | 2524 | 3231 | 1.28 |
| DBC3 | HO-PEG$_{2000}$-PNIPAm | AHP2 | 10:1 | 24 | 5371 | 6846 | 1.27 |
| DBC4 | HO-PEG$_{2000}$-PNIPAm | AHP2 | 10:1 | 48 | 7404 | 9181 | 1.24 |
| DBC5 | HO-PEG$_{2000}$-PNIPAm | AHP2 | 10:1 | 24 | 5583 | 6670 | 1.20 |
| DBC6 | HO-PEG$_{2000}$-PNIPAm | AHP2 | 10:1 | 10 | 4032 | 4717 | 1.17 |
| DBC7 | HO-PEG$_{4000}$-PNIPAm | AHP3 | 10:1 | 24 | 6253 | 7691 | 1.23 |
| DBC8 | HO-PEG$_{4000}$-PNIPAm | AHP3 | 10:1 | 10 | 3794 | 4400 | 1.16 |

The DBCs were then reacted with L-lactide at different feed ratios and/or reaction times to generate several different tri-block copolymers. The second reaction in FIG. 36 is representative of this reaction, where the hydroxyl functional group of the bi-block copolymer initiates the ring-opening polymerization of the L-lactide. These reactions were also performed as described in Example 1. The resulting tri-block copolymers included the PLLA as one end group, the PEG hydrophilic polymer as the middle block, and the PNIPAm as the other end block. Table 3 shows the various example tri-block copolymers, and their corresponding $M_n$, $M_w$, and ratio of $M_w/M_n$ (determined as described herein). Table 3 also shows the di-block copolymer used, the feed mass ratio of the L-lactide to the di-block copolymer, and the reaction time.

TABLE 3

| Tri-Block Copolymer Identifier | Composition | DBC used | Feed Mass Ratio (L-lactide: DBC) | Reaction Time (hours) | $M_n$ | $M_W$ | $M_W/M_n$ |
|---|---|---|---|---|---|---|---|
| TBC1 | PLLA-PEG$_{1000}$-PNIPAm | DBC1 | 3:1 | 24 | 1904 | 2209 | 1.16 |
| TBC2 | PLLA-PEG$_{1000}$-PNIPAm | DBC1 | 5:1 | 24 | 4053 | 4985 | 1.23 |
| TBC3 | PLLA-PEG$_{1000}$-PNIPAm | DBC1 | 5:1 | 24 | 4200 | 4914 | 1.17 |
| TBC4 | PLLA-PEG$_{1000}$-PNIPAm | DBC1 | 10:1 | 24 | 7001 | 9101 | 1.30 |
| TBC5 | PLLA-PEG$_{1000}$-PNIPAm | DBC1 | 15:1 | 24 | 22654 | 31942 | 1.41 |
| TBC6 | PLLA-PEG$_{1000}$-PNIPAm | DBC2 | 10:1 | 24 | 16256 | 22271 | 1.37 |

TABLE 3-continued

| Tri-Block Copolymer Identifier | Composition | DBC used | Feed Mass Ratio (L-lactide: DBC) | Reaction Time (hours) | $M_n$ | $M_W$ | $M_W/M_n$ |
|---|---|---|---|---|---|---|---|
| TBC7 | PLLA-PEG$_{1000}$-PNIPAm | DBC2 | 15:1 | 24 | 21005 | 30247 | 1.44 |
| TBC8 | PLLA-PEG$_{2000}$-PNIPAm | DBC3 | 3:1 | 24 | 6376 | 7286 | 1.14 |
| TBC9 | PLLA-PEG$_{2000}$-PNIPAm | DBC3 | 5:1 | 24 | 8042 | 8726 | 1.09 |
| TBC10 | PLLA-PEG$_{2000}$-PNIPAm | DBC3 | 10:1.5 | 24 | 12584 | 15227 | 1.21 |
| TBC11 | PLLA-PEG$_{2000}$-PNIPAm | DBC3 | 10:1.5 | 24 | 16665 | 23521 | 1.41 |
| TBC12 | PLLA-PEG$_{2000}$-PNIPAm | DBC3 | 15:1 | 24 | 45683 | 68524 | 1.50 |
| TBC13 | PLLA-PEG$_{2000}$-PNIPAm | DBC4 | 10:1 | 24 | 14775 | 22754 | 1.54 |
| TBC14 | PLLA-PEG$_{2000}$-PNIPAm | DBC5 | 15:1 | 24 | 31019 | 45288 | 1.46 |
| TBC15 | PLLA-PEG$_{2000}$-PNIPAm | DBC6 | 15:1 | 24 | 31020 | 44669 | 1.44 |
| TBC16 | PLLA-PEG$_{4000}$-PNIPAm | DBC7 | 15:1 | 24 | 31008 | 48372 | 1.56 |
| TBC17 | PLLA-PEG$_{4000}$-PNIPAm | DBC8 | 3:1 | 24 | 4869 | 5192 | 1.07 |
| TBC18 | PLLA-PEG$_{4000}$-PNIPAm | DBC8 | 5:1 | 24 | 8157 | 13385 | 1.53 |
| TBC19 | PLLA-PEG$_{4000}$-PNIPAm | DBC8 | 10:1 | 24 | 18553 | 26345 | 1.42 |
| TBC20 | PLLA-PEG$_{4000}$-PNIPAm | DBC8 | 15:1 | 24 | 35465 | 44331 | 1.25 |

Synthesis of Microspheres from the Tri-Block Copolymers

Each of the tri-block copolymers was exposed to the two-step self-assembling procedure disclosed herein to generate microspheres. Each of the tri-block copolymers was respectively dissolved in THF at 60° C. with a concentration of 2.0% (w/v). Under rigorous mechanical stirring (speed 7, MAXIMA, Fisher Scientific), glycerol (60° C.) with three times the volume of the PLLA-PEG-PNIPAm copolymer solution was gradually added into the PLLA-PEG-PNIPAm copolymer solution for emulsification and formation of liquid microspheres. Stirring was continued for 5 minutes afterwards. The mixture was then quickly poured into liquid nitrogen. After about 10 minutes, a water ice mixture (1,000 ml) was added for solvent exchange for about 24 hours. The spheres were sieved and washed with an excessive amount of distilled water 6 times to remove glycerol residue. The spheres were then lyophilized for 3 days.

Microsphere Structure/Architecture

The surface morphology of the various copolymer microspheres was examined using scanning electron microscopy (SEM). A Philips XL30 FEG SEM was used with an accelerating voltage of 8 kV. The samples were coated with gold for 90 seconds using a sputter coater (DeskII, Denton vacuum Inc.). During the coating process, the gas pressure was kept at 50 mtorr and the current was 18 mA.

All of the copolymer generated some form of microsphere, but not all of the microspheres were nano-fibrous. Representative examples of the microsphere structures are discussed herein. The microspheres had diameters ranging from about 10 μm to about 100 μm. The sphere size may be affected by the polymer chemical structure, the emulsion strength (which may be controlled by stirring), the temperature of the emulsion, and the medium used. Sieves may be used to obtain a narrower size range if that is desirable.

TBC8 (total $M_n$ of about 6376) was synthesized first using a PEG block with an $M_n$ of about 1550, a PNIPAm block with an $M_n$ of about 3800, and a PLLA block with an $M_n$ of about 1000. As shown in FIG. 8 at A1 through C1, the microspheres formed with tri-block copolymer TBC8 had a smooth surface instead of a nano-fibrous structure. The failure to form the nano-fibrous feature was attributed to the short chain length of the PLLA.

By controlling the PEG-PNIPAm/L-lactide ratio in the ring opening polymerization of L-lactide, TBC9 (total $M_n$ of about 8042) was synthesized with the identical PEG ($M_n$=~1550) and PNIPAm ($M_n$=~3800) lengths and an increased PLLA length ($M_n$=~2700). The microspheres made of the TBC9 copolymer had a platelet-like morphology, as shown in FIG. 8 at A2 through C2.

The $M_n$ of the PLLA block was further increased to ~11300 in TBC11 (total $M_n$ of about 16665). With this PLLA block, microspheres with a nano-fibrous structure were fabricated, as shown in FIG. 8, at 3A through 3C. The average diameter of the nanofibers in the microspheres was about 150 nm, which is in the same size range as collagen fibers. The average fiber diameter was calculated from the SEM micrographs. At least 100 fibers were measured for each sample, and their averages and standard deviations were determined.

These results indicate that, after careful tuning of the chemical structure, PLLA-PEG-PNIPAm tri-block copolymers can successfully self-assemble into nano-fibrous microspheres.

Using the microspheres fabricated with TBC11 as an example, it was discovered that as the microspheres increased in diameter, one open hole or multiple open holes formed at the exterior surface of the microsphere. Examples are shown in FIGS. 9A through 9F. FIGS. 9A through 9C are SEM images of TB11 microspheres with no open hole, one open hole, and multiple open holes, respectively. FIGS. 9D through 9E are 2D cross-sectional fluorescence micrographs (reproduced in black and white) of the microspheres respectively shown in FIGS. 9A through 9C. As shown in FIGS.

9A through 9F, one open hole or multiple open holes were achieved when the diameter of microspheres was larger than about 30 μm.

TB11 microspheres with different diameters were examined to determine whether there was a trend between pore number and diameter. 100 microspheres for each diameter were examined under SEM and the pore number was manually counted. FIG. 10 illustrates a graph that shows the relationship between the average pore number on one side of the microsphere versus the diameter. Clearly, the number of pores on one side increased as the diameter of the microspheres increased. More specifically, the average number of open holes on one side of the nano-fibrous microspheres increased from 0 to more than 20 when the diameter increased from about 10 μm to 100 μm.

Tri-Block Copolymer Distribution in the Microspheres

To examine the distribution of PLLA, PNIPAm and PEG blocks in PLLA-PEG-PNIPAm nanofibrous microspheres, examples were prepared in which each of the blocks was individually and chemically stained with a fluorescent monomer.

Synthesis of Br-PEG-PLLA copolymer: Dry THF (10 mL), L-lactide (139 mmol, 2 g), PEG macroinitiator=1551) (0.6 mmol, 1 g), and Sn(Oct)$_2$ (0.4 mmol, 0.162 g) were mixed in a 50 mL round-bottom flask with stirring and nitrogen purging. The mixture was heated to 80° C. under nitrogen protection for complete melting. The polymerization was carried out at 80° C. under nitrogen protection for 24 hours. The crude product was dissolved in 20 mL THF, and precipitated in 100 mL de-ionized (DI) water. The resulting mixture was then dialyzed (MW cut-off 3.5 kDa) against de-ionized water for 3 days to remove unreacted PEG-macroinitiator. The mixture was then lyophilized for three days to give Br-PEG-PLLA copolymer.

Synthesis of fluorescein o-acrylate stained PLLA-PEG copolymer: The Br-PEG-PLLA copolymer (1 g), Fluorescein o-acrylate (0.065 mmol, 0.025 g), and CuCl (0.170 mmol, 0.016.8 g) were placed in a 250 mL round-bottom flask under nitrogen protection and sealed with rubber septum stoppers. Milli-Q water (20 mL) and Me$_6$TREN (0.174 mmol, 0.04 g) were placed in a Schlenk tube and purged with N$_2$ gas for 40 minutes. The solution was transferred to the round-bottom flask using a syringe under nitrogen protection. The reaction mixture was then stirred under nitrogen atmosphere for about 24 hours. The reaction was then stopped by opening the vessel to air. The reaction mixture was dialyzed (MW cut-off 3.5 kDa) against DI water for 3 days to remove unreacted Fluorescein o-acrylate. The mixture was then lyophilized for three days to give fluorescein o-acrylate stained PLLA-PEG copolymer.

Synthesis of Fluorescein o-acrylate (PEG) and acryloxyethyl thiocarbamoyl Rhodamine B (PNIPAm) stained PLLA-PEG-PNIPAm copolymer: Fluorescein o-acrylate stained PLLA-PEG copolymer (0.5 g), acryloxyethyl thiocarbamoyl Rhodamine B (0.007 mmol, 0.005 g), NIPAm (26.5 mmol, 3 g) and CuCl (0.170 mmol, 0.016.8 g) were placed in a 250 mL round-bottom flask under nitrogen protection and sealed with rubber septum stoppers. Milli-Q water (20 mL) and Me$_6$TREN (0.174 mmol, 0.04 g) were placed in a Schlenk tube and purged with N$_2$ gas for 40 minutes. The solution was transferred to the round-bottom flask using a syringe under nitrogen protection. The reaction mixture was then stirred under nitrogen atmosphere for 24 hours. The reaction was then stopped by opening the vessel to air. The reaction mixture was dialyzed (MW cut-off 3.5 kDa) against DI water for 3 days to remove unreacted acryloxyethyl thiocarbamoyl Rhodamine B. The mixture was then lyophilized for three days to give Fluorescein o-acrylate and acryloxyethyl thiocarbamoyl Rhodamine B stained PLLA-PEG-PNIPAm copolymer.

Synthesis of Nile blue acrylamide stained PLLA polymer: HEMA-PLLAS (1.4 g), Nile blue acrylamide (0.012 mmol, 0.005 g), and AIBN (0.06 mmol, 9.8 mg) were added into dioxane (10 mL) and stirred until dissolved. The polymerization was carried out at 70° C. for 24 h. After polymerization, the crude product was purified by repeated re-precipitations from chloroform to methanol for 3 times, and finally vacuum dried at 40° C. for 48 h to give Nile blue acrylamide stained PLLA polymer.

Fabrication of florescence stained nanofibrous microspheres: TBC11 in Table 3 was dissolved in 20 mL THF at 60° C. with a concentration of 2.0% (wt/v). Fluorescein o-acrylate and acryloxyethyl thiocarbamoyl Rhodamine B stained PLLA-PEG-PNIPAm copolymer (0.1 g) and Nile blue acrylamide stained PLLA polymer (0.05 g) were added and dissolved. Under rigorous mechanical stirring (speed 7, MAXIMA, Fisher Scientific), glycerol (60° C.) with three times the volume of the PLLA-PEG-PNIPAm copolymer solution was gradually added into the PLLA-PEG-PNIPAm copolymer solution. Stirring was continued for 5 minutes afterwards. The mixture was then quickly poured into liquid nitrogen. After 10 minutes, a water ice mixture (1,000 ml) was added for solvent exchange for 24 hours. The spheres were sieved and washed with an excessive amount of distilled water six times to remove glycerol residue. The spheres were then lyophilized for three days.

Confocal imaging was used to observe these microspheres. The microspheres were treated with 10% w/v rhodamine-conjugated BSA aqueous solution for 20 minutes, followed with extensive washing using deionized water. The microspheres were examined using confocal laser scanning microscopy (CLSM) (Nikon Eclipse C1).

FIGS. 11A through 11D are black and white reproductions of 2D cross-section confocal fluorescence micrographs that were originally in color. In the original colored micrograph corresponding with FIG. 11A, the microsphere was red, indicative of the PNIPAm block that was stained red by acryloxyethyl thiocarbamoyl rhodamine B (red). In the original colored micrograph corresponding with FIG. 11B, the microsphere was green, indicative of the PEG block that was stained green by fluorescein o-acrylate. In the original colored micrograph corresponding with FIG. 11C, the microsphere was blue, indicative of the PLLA block that was stained blue by Nile blue acrylamide (blue). FIG. 11D is the merged image of FIGS. 11A, 11B, and 11C. The originals colored images indicated that all three colors, and thus all three blocks were distributed throughout the microspheres. However, when observed at a higher magnification using a high-resolution confocal fluorescence microscope (Leica SP8), the blocks were clearly distinguishable.

FIG. 11E is the higher magnification image of FIG. 11A, FIG. 11F is the higher magnification image of FIG. 11B, FIG. 11G is the higher magnification image of FIG. 11C, and FIG. 11H is the higher magnification image of FIG. 11D. FIG. 11G indicates that the PLLA block formed a typical nanofibrous structure with more defined lines and dots. In contrast, FIGS. 11E and 11F indicate that both PEG (green) and PNIPAm (red) blocks formed diffusive cloud-like structures surrounding the nanofibers. This observation was more obvious when the PLLA block fluorescent micrograph FIG. 11G and the PNIPAm block fluorescent micrograph FIG. 11E were merged, as shown (in black and white) in FIG. 12A. This observation was more obvious when the PLLA block fluorescent micrograph FIG. 11G and the PEG block fluorescent micrograph FIG. 11F were merged, as shown (in black and white) in FIG. 12B. In the original colored version of these respective images, the PLLA fibers are surrounded by PNIPAm (red) (FIG. 12A) or PEG (green) (FIG. 12B) clouds. These results demonstrated that self-assembled PLLA nanofibers with a fiber core-corona structure were formed in the nano-fibrous microspheres, where PEG and PNIPAm blocks became the surrounding two-layer corona (see, e.g., FIG. 3B).

In Vitro Microsphere Degradation

TB11 microspheres within two different size ranges (30-60 μm or 60-90 μm) were examined for in vitro degradation. The in vitro degradation was examined using SEM and weight loss measurement. Degradation is desirable in tissue engineering after tissue has been regenerated.

100 mg of the respective TB11 microspheres were immersed in phosphate buffer solution (PBS, 10 mL, 0.1 M, pH 7.4) on an orbital shaker at 37° C. with a shaking speed of 50 rpm. The buffer solution was renewed every other day. At preset time intervals, the samples were removed from the buffer solution and dried to constant weights under vacuum at room temperature. The morphological changes were examined using SEM.

Prior to incubation in PBS, the TB11 microspheres had a spherical shape with open holes. The 30-60 μm TB11 microspheres prior to incubation are shown in FIG. 13A, and the 60-90 μm TB11 microspheres prior to incubation are shown in FIG. 14A. The 30-60 μm TB11 microspheres after 2 weeks of incubation are shown in FIG. 13B, and the 60-90 μm TB11 microspheres after 2 weeks of incubation are shown in FIG. 14B. As illustrated in each of FIGS. 13B and 14B, most of the TB11 microspheres still had a spherical shape after 2 weeks of incubation, although some of the TB11 microspheres were deformed. After 5 weeks of incubation, even more TB11 microspheres were deformed or disintegrated, as illustrated in FIGS. 13C and 14C. After 8 weeks of incubation, both the 30-60 μm TB11 microspheres (FIG. 13D) and the 60-90 μm TB11 microspheres (FIG. 14D) disintegrated entirely into small pieces.

The degradation of the tri-block copolymers was also compared with PLLA microspheres.

A PLLA homopolymer with a number average molecular weight of 5521 was synthesized by the ring opening polymerization of L-lactide using 2-hydroxyethyl methacrylate (HEMA) as the initiator. The molar percentage of HEMA to L-lactide was 1.25 to 1.00. The L-lactide, HEMA, and Sn(Oct)$_2$ were mixed in a 50 mL round-bottom flask with stirring and nitrogen purging. The mixture was heated to 120° C. under nitrogen protection for complete melting. The polymerization was carried out at 140° C. for 2 hours. The crude product was dissolved in 20 mL chloroform, precipitated in 100 mL cold methanol, and then vacuum dried. PLLA microspheres were then prepared as described herein using dissolution, emulsification using glycerol, and phase separation using liquid nitrogen.

The PLLA microspheres were incubated in PBS and monitored in the same manner as the TB11 microspheres.

FIG. 15 illustrates the degradation results. As shown in FIG. 15, the pure PLLA microspheres (30-60 μm, Mn=~5521) lost only about 11% of the weight after 15 weeks of incubation in PBS. In contrast, the TB11 microspheres with diameters in the range of 30-60 μm and in the range of 60-90 μm lost more than 74% and 62% of their weights, respectively. These results indicate that the introduction of hydrophilic PEG and PNIPAm blocks into PLLA likely enhanced the hydrophilicity and accelerated the degradation compared to PLLA-based nano-fibrous microspheres.

Microsphere Gelation

The TB11 microspheres within the size range of 60-90 μm were evaluated to determine whether they could form a hydrogel. The gelation of the TB11 microspheres was also compared to microspheres of two different di-block copolymers (PLLA-PNIPAm and PLLA-PEG), microspheres of a random copolymer of PLLA, PEG, and PNIPAm, and the PLLA microspheres.

The di-block copolymer PLLA-PEG (89:11 weight ratio) was prepared using OH-PEG-Br as the initiator for the ring opening polymerization of L-lactide. The reaction took place in THF with Sn(Oct)$_2$ at 80° C.

The di-block copolymer PLLA-PNIPAm (73:27 weight ratio) was prepared using 2-(2-bromoisobutyryloxy)ethyl methacrylate) as a double-headed initiator for the atom transfer radical polymerization of NIPAm and for the ring opening polymerization of L-lactide. 2-(2-bromoisobutyryloxy)ethyl methacrylate) was reacted with NIPAm in a water/ethanol mixture with copper chloride (CuCl) and tris-[2-(dimethylamino)ethyl]amine (Me6) at room temperature. Then, the ROP of L-lactide was performed in THF with Sn(Oct)$_2$ at about 80° C.

The random copolymer of PLLA, PEG, and PNIPAm did not have three distinct blocks along the copolymer chain, but rather, the respective polymers were randomly distributed along the copolymer chain. For the random copolymer, a poly(ethylene glycol) methacrylate (PEGM) and PLLA macromonomer was first synthesized as follows: L-lactide (40 mmol, 5.760 g), PEGMA (4 mmol, 2.0 g) and Sn(Oct)$_2$ (0.4 mmol, 0.162 g) were mixed in a 50 mL round-bottom flask with stirring and nitrogen purging. The mixture was heated to 120° C. under nitrogen protection for complete melting. The polymerization was carried out at 140° C. for 2 hours. The crude product was dissolved in 20 mL chloroform, precipitated in 100 mL cold methanol, and then vacuum dried. PLLA-PEG-PNIPAm random copolymer was synthesized as follows: PEGMA-PLLA macromonomer (1.4 g), PEGMA (2 mmol, 0.1 g), NIPAm (12.4 mmol, 1.4 g) and azobisisobutyronitrile (AIBN, 0.06 mmol, 9.8 mg) were added into dioxane (10 mL) and were stirred until dissolved. The polymerization was carried out at 70° C. for 24 hours. After polymerization, the crude product was purified by repeated re-precipitations from chloroform to methanol for 3 times, and finally vacuum dried at 40° C. for 48 hours.

For the PLLA-PEG-PNIPAm random copolymer, the $M_n$=16630 and the $M_w$=24114, as measured by GPC and calculated using polystyrene as standards and THF as the eluent. The mass ratio of PLLA, PEG, and PNIPAm in the random copolymer was 52/14/34 wt %, as calculated from the average signal intensity ratios of methylene protons of PEG, methine protons of PNIPAm, and methine protons of PLLA.

PLLA-PEG microspheres, PLLA-PNIPAm microspheres, random copolymer microspheres, and PLLA microspheres were then prepared as described herein using dissolution, emulsification using glycerol, and phase separation using liquid nitrogen.

Respective aqueous dispersions were prepared with the TB11 microspheres, the two different di-block copolymer microspheres, the random copolymer microspheres, and the PLLA microspheres at 5% w/v. At 25° C., each of the aqueous dispersions was a free-flowing liquid. The temperature of each of the dispersions was raised to 37° C. (e.g., body temperature). At the higher body temperature, the aqueous dispersion including the TB11 microspheres became a 3D hydrogel. The aqueous suspension of TB11 microspheres did not a gel at 25° C., but did form a gel at 37° C. These results illustrate that the tri-block copolymer undergoes thermally induced physical crosslinking at the higher temperature for the hydrogel formation. None of other microspheres formed a hydrogel at the raised temperature. Rather, the PLLA-PEG di-block copolymer microspheres remained in the liquid suspension; the random copolymer microspheres remained in the liquid suspension; the PLLA-PNIPAm di-block copolymer microspheres precipitated out of the suspension, and the PLLA microspheres precipitated out of the suspension. These results show that the water-binding PEG and physical crosslink-forming PNIPAm enable the tri-block copolymer disclosed herein to form a hydrogel.

Figure 16A:
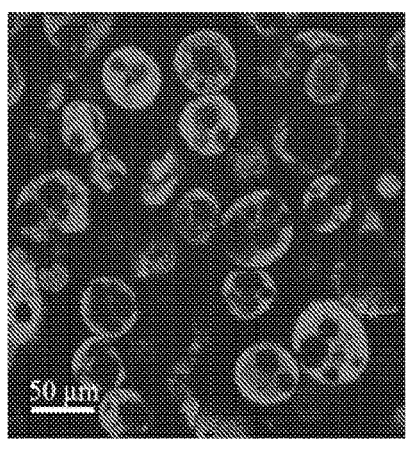
FIG. 16A is a black and white reproduction of a 2D cross-sectional confocal fluorescence micrograph of a hydrogel formed with a 5% w/v aqueous suspension including the microspheres (60 μm to 90 μm in diameter) formed from the tri-block copolymer having PLLA:PEG:PNIPAm=68:9:23.
Figure 16B:
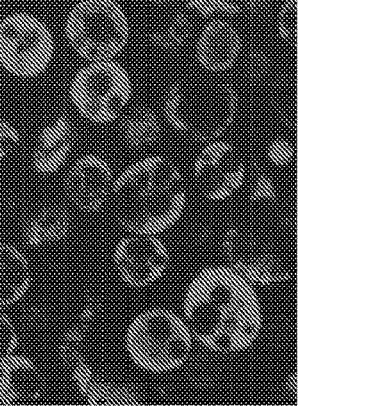
FIG. 16B is a schematic illustration of the crosslinking between the microspheres within the hydrogel of FIG. 16A.
Figure 17:
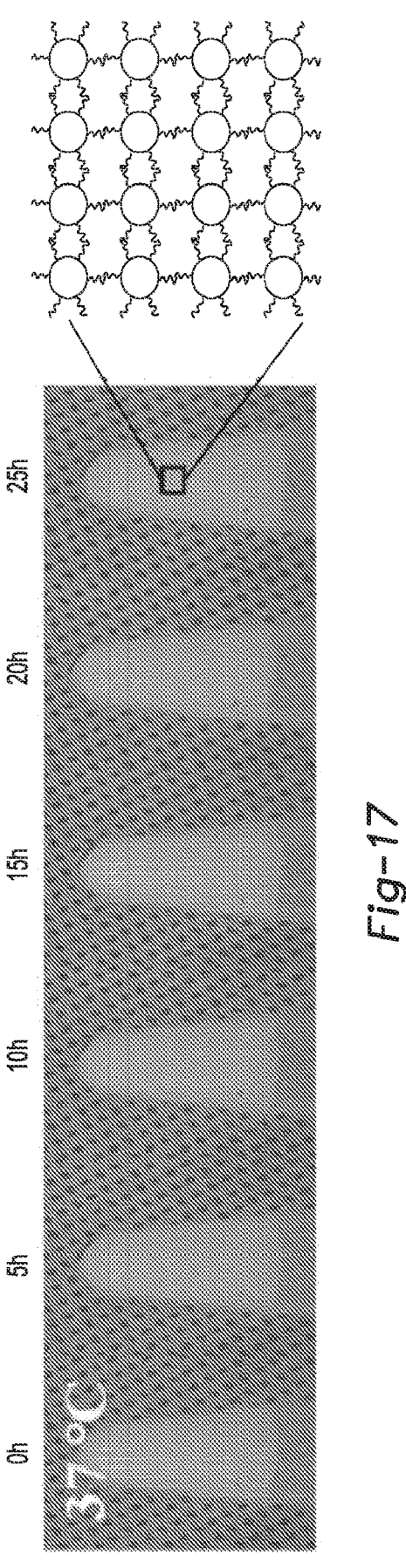
FIG. 17 is a black and white representation of an originally colored photograph demonstrating the stability of the hydrogel formed with the 5% w/v aqueous suspension including the microspheres (60 μm to 90 μm in diameter) formed from the tri-block copolymer having PLLA:PEG.

The TB11 microspheres (60-90 μm, 5% w/v concentration, stained with Rhodamine-BSA) were placed on a heated glass slide, and were observed using confocal laser scanning microscopy. The results are shown in FIG. 16A in black and white, and are reproduced schematically in FIG. 16B. As depicted in both figures, the TB11 microspheres maintained their microsphere structure inside the formed 3D hydrogel. This is unlike other microspheres, which tend to lose their 3D geometry through hydrogel formation. The TBC11 microspheres at 5% w/v concentration in the hydrogel were able to maintain the 3D shape at 37° C. for a long time, as shown in FIG. 17.

Rheological measurements were carried out to measure the sol-gel transition temperature and viscoelastic properties of microspheres formed with TBC6 (PLLA:PEG:PNIPAm=84:5:11), TBC 7 (PLLA:PEG:PNIPAm=88:4:8), and TBC 11 (PLLA:PEG:PNIPAm=68:9:23) (Table 3). The rheological properties, including the storage modulus (G') and the loss modulus G") of the hydrogels w ere monitored using an AR2000 Rheometer (TA instruments, United States) equipped with a temperature controller. Parallel plates with 20 mm diameter were used for all the tests. The gap distance between the plates was 0.4 mm. For measurements other than frequency spectrum, a constant 1 rad/s angular speed was used. For measurements other than stress sweeps, a constant 0.1 Pa stress was used. Temperature sweeps were performed on samples from 20° C. to 45° C. with a heating rate of 2° C./min. Frequency sweeps ranging from 0.1 to 100 rad/s were conducted at 37° C. Stress sweeps were performed on samples from 1 to 1000 Pa at 37° C.

FIGS. 18A through 18C depict the temperature-responsive G' and G" modulus change for the 10% w/v TBC11 aqueous suspension, the 10% w/v TBC6 aqueous suspension, and the 10% w/v TBC7 aqueous suspension, respectively. As depicted in FIG. 18A, the storage modulus (G') of the TBC11 aqueous suspension increased from lower than 10 Pa at 30° C. to 8000 Pa at 45° C., showing the sol-gel transition temperature to be at approximately 35° C. A similar phenomenon was observed for the 10% w/v TBC6 aqueous suspension (FIG. 18B) and for the 10% w/v TBC7 aqueous suspension (FIG. 18C). These results show that TBC7 can form a flowable (not free standing) hydrogel.

To determine the strength and stability of the TB11 microspheres, the stress sweep experiments were performed on the hydrogel of the 10% w/v TBC11 aqueous suspension at 37° C. A linear viscoelastic region (LVR) was observed at the stress level increasing from 0.1 to 20 Pa, as shown in FIG. 19. When the applied stress was increased from 20 to 100 Pa, the storage modulus (G') gradually decreased and the Tan(δ) (G"/G') increased. When the applied stress exceeded 100 Pa, the G' dropped dramatically from 145 to 2 Pa while the Tan(δ) increased from 0.5 to 2.5, indicating a yield stress level and the loss of mechanical integrity.

Once the LVR was determined, frequency sweep experiments at a fix stress (0.1 Pa) were performed with each of the 10% w/v TBC11 (A), TBC6 (B), and TBC 7 (B) aqueous suspension at 37° C. with rheological frequency increasing from 0.1 to 100 rad/s. As shown in FIGS. 20 and 21, the modulus showed frequency independence, and G' was dominant over G" in the entire frequency range.

The results in FIG. 20 illustrate the effect of PNIPAm percentage on the hydrogel strength. As noted above, TBC6 had 11 wt % PNIPAm, TBC 7 had 8% PNIPAm, and TBC 11 had 23 wt % PNIPAm. TBC 11 (with the highest weight percentage of the temperature-responsive polymer) had the highest G' of 1000 Pa, TBC6 (with 11 wt % of the temperature-responsive polymer) had a G' of 260 Pa, and TBC7 (with the lowest weight percentage of the temperature-responsive polymer) had the lowest G' of 75 Pa. A similar phenomenon was observed for G", showing the positive correlation between the PNIPAm percentage (crosslinking density) and the mechanical properties of the microspheres.

The results in FIG. 21 illustrate the effect of microsphere concentration on the hydrogel mechanical properties. In this test, the TB11 microspheres were tested at two different concentrations, 5% w/v and 10% w/v. As the concentration decreased from 10% to 5% w/v, G' and G" of the hydrogel decreased from 1000 Pa to 300 Pa and 140 Pa to 80 Pa, respectively. These results illustrate the correlation between the microsphere concentration and the mechanical properties of the microsphere hydrogel.

The results of temperature sweep, stress sweep and frequency sweep experiments consistently confirmed that the aqueous suspension of the PLLA-PEG-PNIPAm microspheres is a free-flowing, injectable liquid at room temperature that forms a mechanically useful physical hydrogel at 37° C., with a modulus in the order of magnitude of $10^1$ Pa to $10^3$ Pa depending on both the PNIPAm percentage and microsphere concentration, which can be readily tuned for various biomedical applications.

Example 3

Composition Effect on Microstructure and Gelation of PLLA-PEG-PNIPAm Microspheres The various tri-block copolymers in Table 3 had varying PLLA, PEG, and PNIPAm block lengths. Each of these tri-block copolymers was use to form microspheres using THF and glycerol as described in Example 2. The microstructure and gelation property of these microspheres were also evaluated.

For comparison, linear PLLA homopolymers with three different molecular weights were synthesized (compositions and molecular weights (g/mol) are shown Table 4) and fabricated into microspheres as described in Example 2. The microstructure and gelation property of these microspheres were also evaluated.

TABLE 4

| PLLA homopolymer Identifier | Feed Mass Ratio (HEMA:L-lactide) | $M_n$ | $M_w$ | $M_w/M_n$ |
|---|---|---|---|---|
| PLLA1 | 1.25:100 | 5521 | 6901 | 1.25 |
| PLLA2 | 2.5:100 | 4700 | 5263 | 1.11 |
| PLLA3 | 5:100 | 3803 | 4727 | 1.24 |

The microstructures were observed using SEM. If 90% or more of the microspheres in the observed sample/batch had a nano-fibrous structure, the microstructures were deemed to have the capability of forming the nano-fibers.

The microstructures were also visually observed. If the microspheres (in 5% to 10% w/v aqueous suspensions) were able to form a hydrogel at 37° C., the microstructures were deemed to have the capability of forming a free standing hydrogel.

The microstructure and hydrogel results for all of the tri-block copolymers and the PLLA homopolymers are shown in Table 5.

$M_n$ was increased to about 5521. These results showed that the molecular weight has a critical effect on the PLLA microsphere structure. Thus, for the tri-block copolymers disclosed herein that include a PLLA block, the $M_n$ of PLLA block may be higher than about 5521 so that the resulting microspheres have a desirable nanofibrous structure.

The addition of PEG and PNIPAm blocks to the PLLA block reduces the chain regularity and reduces the crystallinity of the PLLA chains. Therefore, the weight percentage of the PLLA block in the tri-block copolymers disclosed herein may also affect the microsphere structure.

TABLE 5

| Polymer ID | Comp. | $M_n$ | $M_W$ | $M_W/M_n$ | PEG %* | PNIPAm %* | PLLA %* | MS ** | FSH *** |
|---|---|---|---|---|---|---|---|---|---|
| TBC1 | PLLA-PEG$_{1000}$-PNIPAm | 1904 | 2209 | 1.16 | 43 | 26 | 31 | Smooth | Yes |
| TBC2 | PLLA-PEG$_{1000}$-PNIPAm | 4053 | 4985 | 1.23 | 20 | 12 | 68 | Smooth | Yes |
| TBC3 | PLLA-PEG$_{1000}$-PNIPAm | 4200 | 4914 | 1.17 | 19 | 12 | 69 | Platelet | Yes |
| TBC4 | PLLA-PEG$_{1000}$-PNIPAm | 7001 | 9101 | 1.30 | 12 | 7 | 81 | NF | No |
| TBC5 | PLLA-PEG$_{1000}$-PNIPAm | 22654 | 31942 | 1.41 | 3 | 3 | 94 | NF | No |
| TBC6 | PLLA-PEG$_{1000}$-PNIPAm | 16256 | 22271 | 1.37 | 5 | 11 | 84 | NF | Yes |
| TBC7 | PLLA-PEG$_{1000}$-PNIPAm | 21005 | 30247 | 1.44 | 4 | 8 | 88 | NF | No |
| TBC8 | PLLA-PEG$_{2000}$-PNIPAm | 6376 | 7286 | 1.14 | 24 | 60 | 16 | Smooth | Yes |
| TBC9 | PLLA-PEG$_{2000}$-PNIPAm | 8042 | 8726 | 1.09 | 19 | 48 | 33 | Platelet | Yes |
| TBC10 | PLLA-PEG$_{2000}$-PNIPAm | 12584 | 15227 | 1.21 | 6 | 37 | 57 | Platelet | Yes |
| TBC11 | PLLA-PEG$_{2000}$-PNIPAm | 16665 | 23521 | 1.41 | 9 | 23 | 68 | NF | Yes |
| TBC12 | PLLA-PEG$_{2000}$-PNIPAm | 45683 | 68524 | 1.50 | 3 | 9 | 88 | NF | No |
| TBC13 | PLLA-PEG$_{2000}$-PNIPAm | 14775 | 22754 | 1.54 | 10 | 40 | 50 | Platelet | Yes |
| TBC14 | PLLA-PEG$_{2000}$-PNIPAm | 31019 | 45288 | 1.46 | 5 | 13 | 82 | NF | Yes |
| TBC15 | PLLA-PEG$_{2000}$-PNIPAm | 31020 | 44669 | 1.44 | 5 | 8 | 87 | NF | No |
| TBC16 | PLLA-PEG$_{4000}$-PNIPAm | 31008 | 48372 | 1.56 | 9 | 11 | 80 | NF | Yes |
| TBC17 | PLLA-PEG$_{4000}$-PNIPAm | 4869 | 5192 | 1.07 | 57 | 21 | 22 | Smooth | Yes |
| TBC18 | PLLA-PEG$_{4000}$-PNIPAm | 8157 | 13385 | 1.53 | 34 | 13 | 53 | Platelet | Yes |
| TBC19 | PLLA-PEG$_{4000}$-PNIPAm | 18553 | 26345 | 1.42 | 15 | 6 | 79 | NF | No |
| TBC20 | PLLA-PEG$_{4000}$-PNIPAm | 35465 | 44331 | 1.25 | 8 | 3 | 89 | NF | No |
| PLLA1 | | 5521 | 6901 | 1.25 | NA | NA | NA | Platelet | No |
| PLLA2 | | 4700 | 5263 | 1.11 | NA | NA | NA | Initial NF | No |
| PLLA3 | | 3803 | 4727 | 1.24 | NA | NA | NA | NF | No |

*Each weight percent is determined by $Mn_{polymer\ block}/Mn_{TBC}$
**MS = microstructure, NF = nano-fibrous
***FSH = free standing hydrogel The effect of the average molecular weight on the PLLA homopolymers on the microsphere structure was examined. As shown in FIG. 22, at all number average molecular weights, the PLLA homopolymers were fabricated into microspheres. When the $M_n$ of PLLA was about 3803, microspheres with a more platelet structure were fabricated. When the $M_n$ of PLLA increased to about 4700, microspheres with a nanofibrous structure were fabricated. However, some of the fibers were stuck together, which led to an increase of the average fiber diameter. Microspheres with a more desirable nanofibrous structure were fabricated as the FIG. 23 is a graph depicting the PNIPAm percentage (wt %) along the X-axis, the PEG percentage (wt %) along the Y-axis, and the PLLA percentage (wt %) along the Z-axis. For the PLLA block, the minimum weight percentage for nanofiber formation was about 66 wt %. When the weight percentage of PLLA block in the tri-blok copolymers was in the range of about 16 wt % to about 31 wt %, microspheres with a smooth surface were fabricated (see FIG. 23 and Table 1). When the weight percentage of PLLA in the copolymers was in the range of about 31 wt % to about 67 wt %, microspheres with a platelet-like structure were fabricated (see FIG. 23 and Table 1). When the weight percentage of PLLA in the copolymers was about 68 wt % or higher, microspheres with a desirable nano-fibrous structure were fabricated (see FIG. 23 and Table 1). As examples, around 90% of TB11 microspheres (68 wt % PLLA) had a desirable nanofiber structure, whereas about 50% of TBC10 microspheres (57 wt % PLLA) had a desirable nano-fiber structure while the other 50% has the platelet-like structure.

Thus, to fabricate PLLA-PEG-PNIPAm microspheres with a nanofibrous structure, two threshold requirements should be met simultaneously: $M_n$ of the PLLA block should be higher than about 5521 and weight percentage of PLLA block in the copolymers should be 68 wt % or higher. For example, although the $M_n$ of the PLLA block in TBC10 was about 7213 (Tables 3 and 5), the weight percentage of PLLA was only about 57 wt %, and the resulting microspheres had a platelet-like structure. For TBC3, the weight percentage of PLLA was about 69 wt %, but the $M_n$ of the PLLA block was about 2898. The TBC3 microspheres had a platelet-like structure. Only when both the PLLA percentage was 68 wt % or more and the $M_n$ of the PLLA block was about 5521 did the desirable nano-fibrous structure form.

While the results in this example are specific to PLLA, it is to be understood that the minimum weight percentage and the minimum $M_n$ may be different for other hydrophobic, nano-fiber forming polymers.

While it is desirable for the tri-block copolymer to form nano-fibrous microspheres, it is also desirable for it to form a hydrogel when exposed to at least the body temperature. For the PLLA-PEG-PNIPAm tri-block copolymer examples, it has been found that the PEG percentage should be about 5 wt % or higher and the PNIPAm percentage should be about 11 wt % or higher. These percentages may vary for other hydrophilic polymers and/or for other temperature-responsive polymers.

FIG. 24 is a graph depicting the PEG percentage (wt %) along the X-axis, the PNIPAm percentage (wt %) along the Y-axis, and the PLLA percentage (wt %) along the Z-axis. A free-standing hydrogel was achieved when the weight percentage of the PEG block in the tri-block copolymers was 5 wt % or higher. In one example, the PEG block in the tri-block copolymer is in the range of about 5 wt % to about 28 wt % (FIG. 24 and Table 5). When the PEG weight percentage was less than about 5 wt %, precipitation occurred, likely due to the hydrophobic nature of the microspheres. This result demonstrated that about 5 wt % of the PEG block in the PLLA-PEG-PNIPAm copolymers was sufficient to work as the hydrophilic domain to bind water and prevent precipitation from occurring.

FIG. 25 is a graph depicting the PNIPAm percentage (wt %) along the X-axis, the PEG percentage (wt %) along the Y-axis, and the PLLA percentage (wt %) along the Z-axis. A free-standing hydrogel was achieved when the weight percentage of the PNIPAm block in the tri-block copolymers copolymers was about 11 wt % or higher. When the weight percentage of the PNIPAm block in the copolymers was lower than 11 wt %, the hydrophobic interactions between PNIPAm blocks at body temperature was too weak to hold a strong enough physical network, and the PLLA-PEG-PNIPAm microspheres could not form a free-standing hydrogel.

The microstructure and gelation property of the PLLA-PEG-PNIPAm microspheres strongly depend on the copolymer composition. To fabricate nano-fibrous and gel forming microspheres, two threshold requirements should be met simultaneously for the nanofiber formation and two threshold requirements should be met simultaneously for the hydrogel formation. In an example, when the $M_n$ of PLLA block is higher than about 5521, and the weight percentages of PLLA, PEG, and PNIPAm in the tri-block copolymer are 68, 5, and 11 wt % or higher, respectively, the microspheres become nano-fibrous and are capable of forming a free-standing hydrogel at body temperature. These parameters may vary for other hydrophobic, hydrophilic, and temperature-responsive blocks.

Example 4

Heart Regeneration

In Vitro Experiment hESCs (H7 cell line) were differentiated into cardiomyocytes (CMs) using a chemically defined culture. Full confluent single layer hESCs were cultured in CDM3 medium to induce CM differentiation. A lactate medium was applied to purify CMs from day 12 to day 18. At day 20, the derived CMs were digested by trypsin for flow cytometry assay or subsequent transplantation.

To investigate whether the nano-fibrous and gel forming microspheres support cardiomyocytes (CM) maintenance and maturation, the CMs were cultured with the TBC11 microspheres (described in Examples 2 and 3) for 7 days in vitro. 5 million CMs mixed with TB11 microspheres at a ratio of 30:1 were co-cultured in 35 mm petri dishes (Falcon) with CDM3 medium for 7 days.

For immunofluorescence staining, samples were fixed with 4% paraformaldehyde at room temperature for 20 minutes, frozen in Tissue-Plus O.C.T Compound (Fisher Scientific), and cryosectioned into 7 μm sections. Slide sections were permeabilized with 0.3% Triton X-100 for 15 minutes at room temperature, blocked with 5% horse serum in DPBS-T for 1 hour at room temperature and incubated with primary antibodies against cTnT (ab45932, Abcam) at 4° C. overnight in 2% horse serum. Sections were then washed 3 times with PBS for 15 minutes each time, incubated with Alexa Fluor 488-conjugated secondary antibodies (Thermo Fisher Scientific) in 2% horse serum in DPBS-T for 1 hour at room temperature, washed with PBS for 3 times and 15 minutes each time, then stained with DAPI (for nuclei, see FIG. 26A). Images were obtained by fluorescence microscope (Olympus, Japan), and are reproduced in black and white in FIGS. 26A (nuclei staining), 26B (cTnT), and 26C (merged images from 26A and 26B). The open and hollow structure of the TB11 microspheres facilitated CM incorporation, even distribution, and attachment to the gel forming microspheres. The gel formation of the gel forming microspheres prevented CM leakage and allowed CM interactions. Importantly, CMs in the gel expressed cardiac troponin T (FIG. 26B) and maintained the cardiac beating property (data not shown).

In Vivo Experiment

To evaluate the long-term cell retention and engraftment in vivo of the carrier TB11 microspheres, hESC-derived CMs with TB11 microspheres were transplanted into myocardial infarction rats.

Eight-week-old (190-210 g) Female Sprague Daley rats were used, and myocardial infarction was induced by ischemia reperfusion (I/R) surgery. The left anterior descending artery was ligated with 6-0 sutures for 60 minutes and reperfused by loosening the suture. The animals were randomly divided into different groups: PBS control (labeled "PBS" in FIGS. 28 and 30-34B), CM only group (labeled "CM Only" in FIGS. 28 and 30-34B), TBC11 microspheres only group (labeled "NF-GMS" or "TBC11 Microspheres Only" in FIGS. 28 and 30-34B), and CM+ TB11 microspheres group (labeled "CM+NF-GMS" or "CM+TBC11 Microspheres" in FIGS. 28 and 30-34B). For the CM+ TB11 microspheres group, $1\times10^7$ hESC-CMs were mixed with TB11 microspheres at the ratio of 30:1 and were suspended in 100 µl PBS. Seven days after I/R, 100 µl PBS (PBS control group), or 100 µl of a cell suspension containing $1\times10^7$ hESC-CMs (CM only group), or 100 µl of a suspension containing TB11 microspheres (TB11 microspheres only group), or 100 µl of a suspension containing $1\times10^7$ hESC-CMs mixed with TB11 microspheres (CM+ TB11 microspheres group) was injected at 5 sites into the border zone of the infarction. Immunosuppressor cyclosporine A was subcutaneously administered at 10 mg/kg/day from two days before cell transplantation until animals were sacrificed.

The graft size of the transplanted hESC-CMs was assessed at day 28 (4 weeks) after cell transplantation. The hearts were fixed in 4% paraformaldehyde, frozen in Tissue-Plus O.C.T Compound (Fisher Scientific), and cryosectioned into 7 µm sections for immunohistochemistry and histological analyses. For immunofluorescence staining, the procedure was the same as for those in vitro CM+TB11 microspheres samples described above. Staining with primary antibodies against human mitochondrion (MAB1273, EMD Millipore) was performed to identify the transplanted CMs in rat heart. Staining with cTnT (ab45932, Abcam) and Cnnx43 (sc-9059, Santa Cruz Biotechnology) antibodies was performed to characterize CM structure and cell-cell connection. After staining, slides were mounted using Pro-Long® Diamond Antifade Mountant (P36970, Thermo Fisher Scientific) and imaged using a Nikon A1 Confocal Laser Microscope. Staining with anti-CD31 (sc-1506, Santa Cruz Biotechnology) antibody was used to investigate vascular density. In addition, Masson's Trichrome staining was performed to calculate the infarct size in rat hearts.

FIG. 27A illustrates (in black and white) the human specific antigen (Hu-mito) staining image for the CM only group. In this image, CMs were observed mainly in the infarct border zone and occasionally in the infarct zone. FIG. 27B illustrates (in black and white) the human specific antigen (Hu-mito) staining image for the CM+TB11 microspheres group (labeled CM+NF-GMS (nano-fibrous-gelling microsphere). In the CM+ NF-GMS group, much larger and confluent CM grafts were identified predominantly in both the border zone and the infarct zone.

The graft volume was calculated by combining the stained slides every 0.5 mm away from the apex to the base of the heart. The graft area in each slide was measured by Image? software. The results for the Engraft size (in mm³) are shown in FIG. 28. As shown in FIG. 28, there was a significantly higher graft size in the CM+TB11 microspheres group than in the CM only group, indicating an approximately 10-fold graft size increase in infarcted rat heart in the CM+TB11 microspheres group over the CM only group.

The large engraftment of CMs carried by the TB11 microspheres was also detected using immunofluorescence staining against cTnT and anti-Hu-mito staining, as illustrated in FIGS. 29A through 29C. Furthermore, abundant gap junctions between host and transplanted cells (arrows, FIG. 29F) and among transplanted cells were formed as indicated by Connexin 43 staining (FIGS. 29D and 29F), indicating that the TB11 microspheres carried cell transplantation also promoted cell-cell integration between host and transplanted CMs.

The long-term survival and integration of transplanted CMs would require adequate vascular network support in the engrafted areas. Therefore, the vascular density in the infarction border zone and the remote zone (non-infarct zone) in the infarcted rat heart were evaluated by staining with endothelial cell marker CD31 28 days after cell transplantation. Confocal images were obtained and the results are shown in black and white in FIG. 30. In the border zone, the heart treated with the TB11 microspheres illustrated the most CD31 endothelial cells (compared to the other treated hearts) on the lumen surface of the vessels, indicating adequate vascular network support.

The number of vessel-like lumens was calculated to assess the vascular density, and the results for the remote zone are shown in FIG. 31A and the results for the border zone are shown in FIG. 31B. As depicted, in these figures, vascular density in the remote zone was greater than in the border zone in all groups 28 days after cell transplantation. No statistical significance of vascular density was observed in the remote zone among PBS control group, CM only group, TB11 microspheres only group, and CM+TB11 microspheres group. In contrast, a significantly higher vascular density was observed in the border zone of the CM+TB11 microspheres group (397.82±18.15) than those of the CM only group (317.79±21.14) and PBS control group (239.32±16.35) (P<0.01). Thus, the TB11 microspheres carried CM transplantation promoted revascularization in the border zone of the infarcted rat heart.

Masson's Trichrome staining was performed to identify (originally blue) scar tissue and (originally red) live tissue. These images are shown in FIG. 32 in black and white. Live tissue was hardly observed in the infarcted areas of the PBS Control group and the TBC11 microspheres only group. Some clusters of live cells could be found in the CM only group but were mainly near the border zone. In contrast, large clusters of live cells were identified in both border zone and infarct zone in the CM+TB11 microspheres group, leading to a much thicker ventricle wall. As shown in FIG. 33, one month after TB11 microsphere carried CM injection, the infarct size in the CM+TB11 microspheres group was only 16% of the left ventricle of the heart, leading to a 58% reduction compared to the PBS control group, 50% reduction compared to TB11 microspheres only group, and a 43% reduction compared to CM only group (P<0.01).

Echocardiography was performed at day 6 and day 35 to evaluate cardiac function. Left ventricular end-diastolic dimension (LVEDD) and left ventricular end-systolic dimension (LVESD) were measured using a VEVO® 2100 system. Left ventricle ejection fractions (EF) and fractional shortening (FS) were calculated using the equations:

$$EF\ (\%)=(LVEDD^2-LVESD^2)/LVEDD^2\times100\%;\ and$$

$$FS\ (\%)=(LVEDD-LVESD)/LVEDD\times100\%.$$

The echocardiography performed at day 6 to get the infarction baseline before cell transplantation and myocardial infarction in all groups was confirmed with LVFS to be less than 35%. The EF and FS data at day 35 are shown in FIGS. 34A and 34B, respectively. As depicted, a significant increase in cardiac function was found in the CM+TB11 microspheres group with EF of 54.00% and FS of 29.29%, indicating a striking functional recovery with 39% increase in EF and 46% increase in FS compared to PBS control group (P<0.01). The cardiac function of CM+TB11 microspheres group was also significantly greater than that of CM only group with a 17% higher EF and 22% higher FS (P<0.05).

All of the data in this example illustrates that the CM+TB11 microspheres substantially reduced infarct size and enhanced functional recovery compared to CM only transplantation.

The microspheres disclosed herein, which integrate the ECM-mimicking nano-fibrous architecture with a temperature-responsive in situ gel forming property, are an attractive microcarrier for tissue regeneration and drug delivery. As a cell carrier, nano-fibrous microspheres are able to enhance cell retention, survival/proliferation, CM phenotype expression, and integrative heart tissue regeneration. In Example 4, a strikingly 10-fold graft size increase was observed with the microspheres 28 days after CM transplantation in an infarcted rat model. Consequently, the nano-fibrous microsphere-carried CM transplantation has led to dramatically reduced infarct size, increased vasculature in the regenerated areas, coupling of host and transplanted cells, and ultimately, substantially improved heart function.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range, as if such value or sub-range were explicitly recited. For example, a range from about 10% to about 89% should be interpreted to include not only the explicitly recited limits of from about 10% to about 89%, but also to include individual values, such as 25%, 34.5%, 68%, etc., and sub-ranges, such as from about 30% to about 65%, from about 50% to about 85%, etc. Furthermore, when "about" is utilized to describe a value, this is meant to encompass minor variations (up to +/−10%) from the stated value.

In describing and claiming the examples disclosed herein, the singular forms "a", "an", and "the" include plural referents unless the context clearly dictates otherwise.

While several examples have been described in detail, it is to be understood that the disclosed examples may be modified. Therefore, the foregoing description is to be considered non-limiting.

What is claimed is:

1. A tri-block copolymer, comprising:
a first end block consisting of a hydrophobic, nano-fiber forming polymer, wherein the first end block is present in the tri-block copolymer at a weight percentage ranging from about 68% to about 84%, and wherein the hydrophobic, nano-fiber forming polymer is selected from the group consisting of poly(L-lactic acid), poly (lactide-co-glycolide), polyglycolide, polyanhydrides, poly(ortho ethers), polycaprolactone, poly(hydroxy butyrate), poly(phosphoesters), poly(glycerol sebacate), poly(propylene fumarate), polyphosphazenes, polycarbonates, polyurethanes, non-water-soluble collagen, non-water-soluble gelatin, non-water-soluble elastin, and copolymers thereof;
a middle block attached to the first end block, the middle block consisting of a hydrophilic polymer, wherein the middle block is present in the tri-block copolymer at a weight percentage ranging from about 5% to about 9%; and
a second end block attached to the middle block, the second end block consisting of a temperature-responsive polymer, wherein the second end block is present in the tri-block copolymer at a weight percentage ranging from about 11% to about 23%.

2. The tri-block copolymer as defined in claim 1 wherein:
the hydrophilic polymer is selected from the group consisting of poly(ethylene glycol), poly(vinyl alcohol), poly(2-hydroxyethyl methacrylate), polyvinylpyrrolidone, alginate, collagen, gelatin, hyaluronic acid, starch, glycogen, cellulose, carrageenan, dextran, chitin, chitosan, pectin, heparin, heparan sulfate, poly (acrylic acid), poly(acrylamide), poly(N,N'-methylenebisacrylamide), polyvinyl methyl ether, and copolymers thereof.

3. The tri-block copolymer as defined in claim 2 wherein:
the temperature-responsive polymer is switchable from a hydrophilic state to a more hydrophobic state in water when exposed to a predetermined temperature; and
the temperature-responsive polymer is selected from the group consisting of poly(N-isopropylacrylamide), poly [2-(dimethylamino)ethyl methacrylate], hydroxypropylcellulose, poly(vinylcaprolactame), and polyvinyl methyl ether.

4. The tri-block copolymer as defined in claim 2 wherein:
the temperature-responsive polymer is switchable from a soluble state to an insoluble state in an organic solvent when exposed to a predetermined temperature; and
the temperature-responsive polymer is selected from the group consisting of polystyrene, polyethylene, polymethylmethacrylate, and polypropylene.

5. The tri-block copolymer as defined in claim 1 wherein the hydrophobic, nano-fiber forming polymer has a number average molecular weight at or above a nano-fiber formation threshold molecular weight.

6. The tri-block copolymer as defined in claim 5 wherein the hydrophobic, nano-fiber forming polymer is poly(L-lactic acid) and wherein the number average molecular weight is at least 5,500 g/mol.

7. The tri-block copolymer as defined in claim 1 wherein:
the hydrophobic, nano-fiber forming polymer is poly(L-lactic acid);
the hydrophilic polymer is poly(ethylene glycol); and
the temperature-responsive polymer is poly(N-isopropylacrylamide).

8. A method, comprising:
synthesizing an asymmetrical hydrophilic polymer having two different functional end groups, thereby forming a middle block of a tri-block copolymer;
polymerizing a hydrophobic monomer using a first of the two different functional end groups, thereby forming a first end block of the tri-block copolymer attached to the middle block; and
polymerizing a temperature-responsive monomer using a second of the two different functional end groups, thereby forming a second end block of the tri-block copolymer attached to the middle block;
wherein:
the first end block consists of a hydrophobic, nano-fiber forming polymer;
the hydrophobic, nano-fiber forming polymer is selected from the group consisting of poly(L-lactic acid), poly(lactide-co-glycolide), polyglycolide, polyanhydrides, poly(ortho ethers), polycaprolactone, poly(hydroxy butyrate), poly(phosphoesters), poly(glycerol sebacate), poly(propylene fumarate), polyphosphazenes, polycarbonates, polyurethanes, non-water-soluble collagen, non-water-soluble gelatin, non-water-soluble elastin, and copolymers thereof;

the first end block is present in the tri-block copolymer at a weight percentage ranging from about 68% to about 84%;

the middle block consists of a hydrophilic polymer;

the middle block is present in the tri-block copolymer at a weight percentage ranging from about 5% to about 9%;

the second end block consists of a temperature-responsive polymer; and the second end block is present in the tri-block copolymer at a weight percentage ranging from about 11% to about 23%.

9. The method as defined in claim 8 wherein the polymerization of the hydrophobic monomer occurs before, simultaneously with, or after the polymerization of the temperature-responsive monomer.

10. The method as defined in claim 8, further comprising causing the tri-block copolymer to self-assemble into nanofibrous gelling microspheres by:

dissolving the tri-block copolymer to form a solution;

emulsifying the solution to form liquid microspheres; and inducing phase separation of the liquid microspheres.

11. The method as defined in claim 8, further comprising polymerizing a sufficient amount of the hydrophobic monomer to form the first end block with a number average molecular weight at or above a nano-fiber formation threshold molecular weight.

12. A method, comprising:

synthesizing an asymmetrical hydrophilic polymer having two different functional end groups, thereby forming a middle block of a tri-block copolymer, the middle block consisting of the asymmetrical hydrophilic polymer;

conjugating a first end block to the middle block through a first of the two different functional end groups, the first end block consisting of a hydrophobic, nano-fiber forming polymer; and conjugating a second end block to the middle block through a second of the two different functional end groups, the second end block consisting of a temperature-responsive polymer, wherein:

the hydrophobic, nano-fiber forming polymer is selected from the group consisting of poly(L-lactic acid), poly(lactide-co-glycolide), polyglycolide, polyanhydrides, poly(ortho ethers), polycaprolactone, poly(hydroxy butyrate), poly(phosphoesters), poly(glycerol sebacate), poly(propylene fumarate), polyphosphazenes, polycarbonates, polyurethanes, non-water-soluble collagen, non-water-soluble gelatin, non-water-soluble elastin, and copolymers thereof;

the first end block is present in the tri-block copolymer at a weight percentage ranging from about 68% to about 84%;

the middle block is present in the tri-block copolymer at a weight percentage ranging from about 5% to about 9%; and the second end block is present in the tri-block copolymer at a weight percentage ranging from about 11% to about 23%.

13. The method as defined in claim 12 wherein the conjugation of the first end block occurs before, simultaneously with, or after the conjugation of the second end block.

14. The method as defined in claim 12, further comprising causing the tri-block copolymer to self-assemble into nanofibrous gelling microspheres by:

dissolving the tri-block copolymer to form a solution;

emulsifying the solution to form liquid microspheres; and inducing phase separation of the liquid microspheres.

15. The method as defined in claim 12, further comprising polymerizing a sufficient amount of a hydrophobic monomer to form the hydrophobic, nano-fiber forming polymer with a number average molecular weight at or above a nano-fiber formation threshold molecular weight.

16. A nano-fibrous gelling microsphere, comprising:

interconnected nanofibers of the tri-block copolymer of claim 1; and spaces formed between the interconnected nanofibers;

wherein the nano-fibrous gelling microsphere is suspendable in a liquid at a first temperature and is to form a hydrogel in the liquid at a second temperature that is higher than the first temperature.

17. A suspension, comprising:

a liquid carrier;

a plurality of the nano-fibrous gelling microspheres as defined in claim 16; and a plurality of cells or biologically functional molecules attached to at least some of the plurality of the nano-fibrous gelling microspheres or mixed in the liquid carrier with the plurality of the nano-fibrous gelling microspheres.

18. A treatment method, comprising:

introducing the nano-fibrous gelling microspheres as defined in claim 16 into an aqueous solution at a temperature that is below a body temperature, thereby forming a suspension; and injecting the suspension into a heart, in bone, smooth muscle, blood vessel, heart valve, cardiac muscle, skeletal muscle, bladder, tendon, ligament, skin, fat, cartilage, intervertebral disc, breast, liver, intestine, esophagus, trachea, lung, or nerve.

19. The tri-block copolymer as defined in claim 1, wherein the hydrophobic, nano-fiber forming polymer is selected from the group consisting of poly(L-lactic acid), poly(lactide-co-glycolide), polyglycolide, polyanhydrides, poly(ortho ethers), poly(phosphoesters), poly(propylene fumarate), polyphosphazenes, polycarbonates, polyurethanes, non-water-soluble collagen, non-water-soluble gelatin, non-water-soluble elastin, and copolymers thereof.

* * * * *